(12) United States Patent
Hoftman et al.

(10) Patent No.: US 10,569,038 B2
(45) Date of Patent: Feb. 25, 2020

(54) DUAL LUMEN ENDOBRONCHIAL TUBE DEVICE

(71) Applicant: THE REGENTS OF THE UNIVERSITY OF CALIFORNIA, Oakland, CA (US)

(72) Inventors: Nir Hoftman, Los Angeles, CA (US); Aman Mahajan, Sherman Oaks, CA (US); Mike Hoftman, Chatsworth, CA (US)

(73) Assignee: The Regents of the University of California, Oakland, CA (US)

( * ) Notice: Subject to any disclaimer, the term of this patent is extended or adjusted under 35 U.S.C. 154(b) by 510 days.

(21) Appl. No.: 15/340,653

(22) Filed: Nov. 1, 2016

(65) Prior Publication Data

US 2017/0043111 A1    Feb. 16, 2017

Related U.S. Application Data

(63) Continuation-in-part of application No. 13/829,509, filed on Mar. 14, 2013, now Pat. No. 9,687,621.
(Continued)

(51) Int. Cl.
*A61M 16/04* (2006.01)
*A61M 16/08* (2006.01)
*A61M 16/00* (2006.01)

(52) U.S. Cl.
CPC .... *A61M 16/0486* (2014.02); *A61M 16/0445* (2014.02); *A61M 16/0459* (2014.02); *A61M 16/0833* (2014.02); *A61M 2016/003* (2013.01); *A61M 2016/0027* (2013.01); *A61M 2205/3331* (2013.01); *A61M 2205/3368* (2013.01)

(58) Field of Classification Search
CPC .............. A61M 16/04; A61M 16/0402; A61M 16/0404; A61M 16/042; A61M 16/0434; A61M 16/044; A61M 16/0445; A61M 16/0454; A61M 16/0459; A61M 16/0475; A61M 16/0484; A61M 16/0486; A61M 25/1011; A61M 2039/082
See application file for complete search history.

(56) References Cited

U.S. PATENT DOCUMENTS 3,884,242 A * 5/1975 Bazell .................. A61M 16/04
                                                 128/207.14
4,233,984 A * 11/1980 Walling ................ A61M 16/04
                                                 128/207.14
(Continued)

FOREIGN PATENT DOCUMENTS

WO    WO-2014159522 A1 * 10/2014 ........ A61M 16/0816

*Primary Examiner* — Tan-Uyen T Ho
*Assistant Examiner* — Joseph D. Boecker
(74) *Attorney, Agent, or Firm* — Riverside Law LLP

(57) ABSTRACT

The present invention provides improved dual lumen endobronchial tube devices. The dual lumen endobronchial tube devices feature a universal design for left or right mainstem bronchus insertion. The dual lumen endobronchial tube devices also feature enhanced balloon cuff designs to minimize dislodgement while maintaining proper airway sealing. The present invention also includes water activated lubricious coating inside the shaft to reduce friction during insertion of a bronchoscope into the airway. The present invention also provides improved double clamps that prevent the accidental clamping of both tubes of a Y-adapter.

18 Claims, 24 Drawing Sheets

Related U.S. Application Data

(60) Provisional application No. 62/285,592, filed on Nov. 3, 2015, provisional application No. 61/690,867, filed on Jul. 6, 2012.

(56) References Cited

U.S. PATENT DOCUMENTS

| | | | |
|---|---|---|---|
| 9,687,621 B2* | 6/2017 | Hoftman | A61M 16/0816 |
| 2003/0136413 A1* | 7/2003 | Brain | A61M 16/04 128/207.15 |
| 2006/0201516 A1* | 9/2006 | Petersen | A61M 16/04 128/207.14 |
| 2006/0212022 A1* | 9/2006 | Gellman | A61M 25/0097 604/509 |
| 2008/0078402 A1* | 4/2008 | Mongeon | A61M 16/04 128/207.15 |
| 2010/0163023 A1* | 7/2010 | Singh | A61M 16/04 128/200.26 |
| 2011/0186053 A1* | 8/2011 | Pol | A61B 1/00045 128/207.15 |
| 2012/0024292 A1* | 2/2012 | Sandmore | A61M 16/04 128/207.14 |
| 2013/0158351 A1* | 6/2013 | Daher | A61M 16/04 600/109 |
| 2017/0232216 A1* | 8/2017 | Nave | A61B 1/267 600/120 |

* cited by examiner

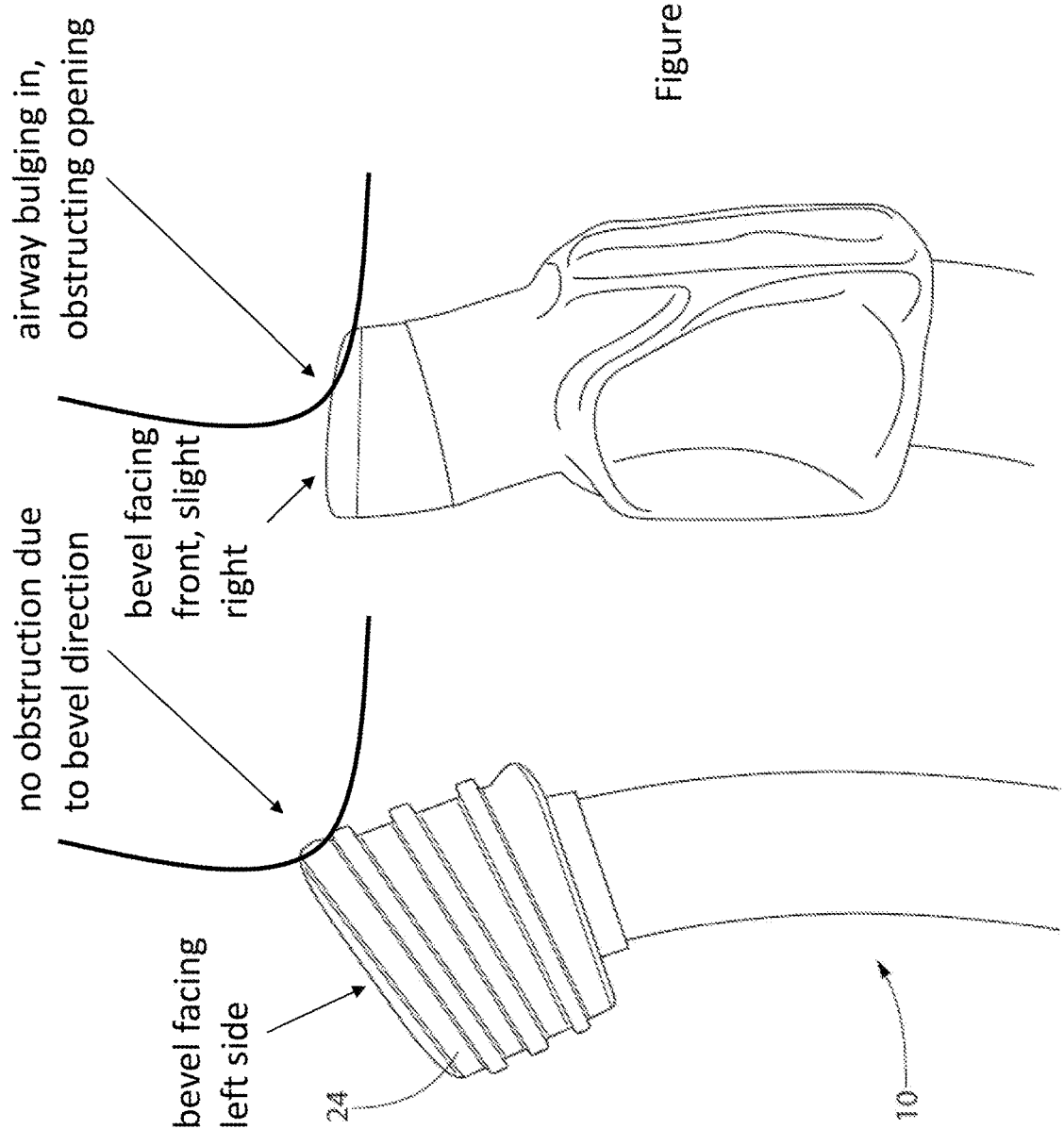

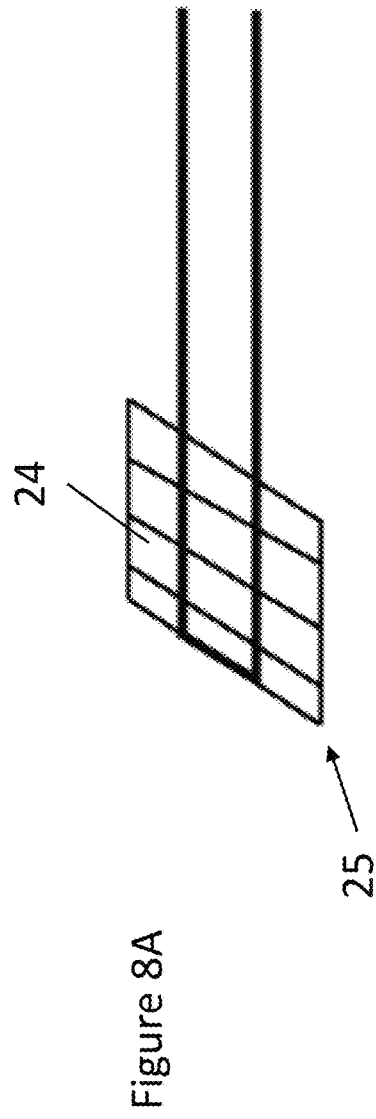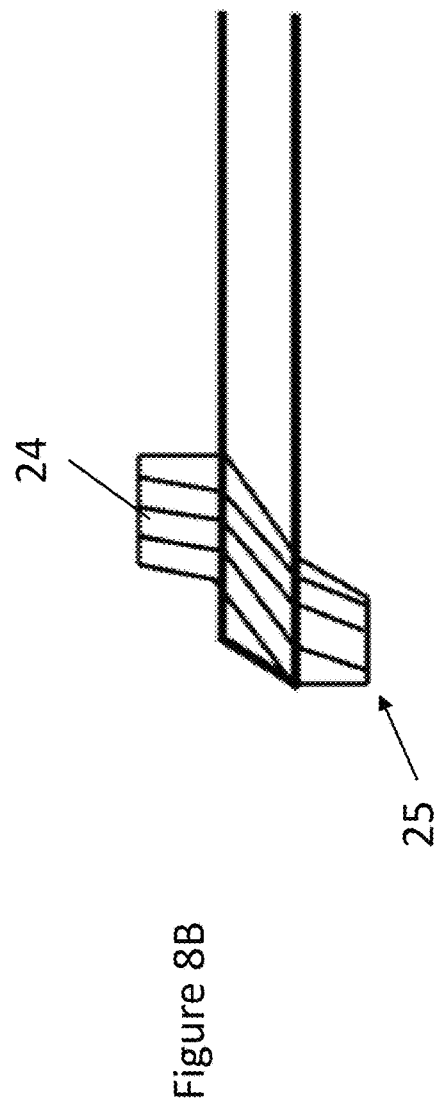
Figure 8A
Figure 8B
Figure 8A – Figure 8B

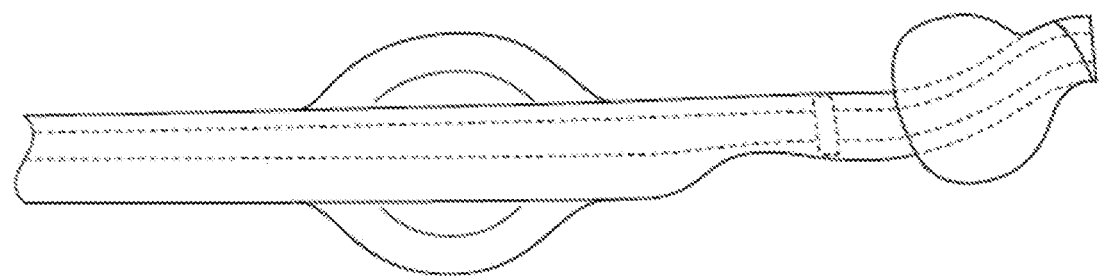
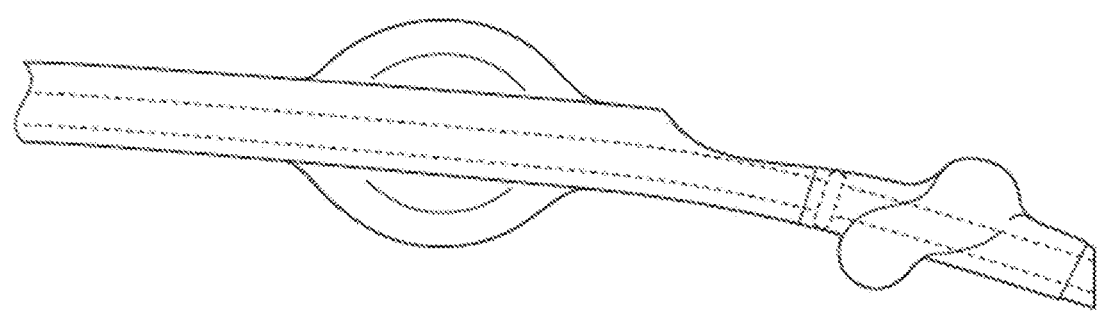
Figure 12

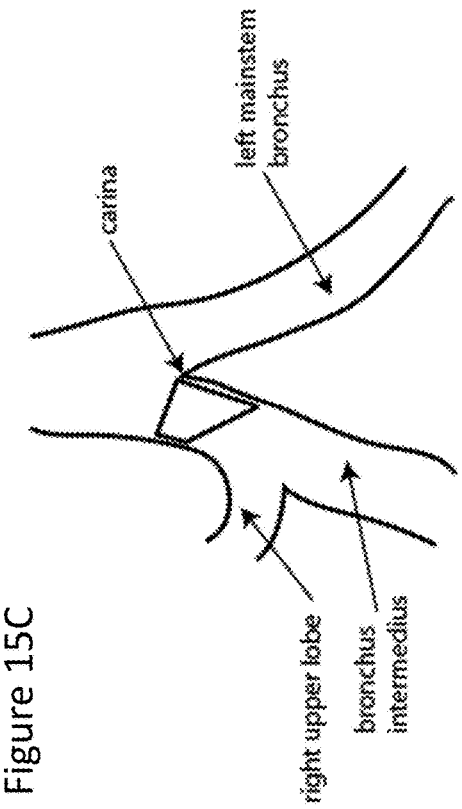
Figure 15C
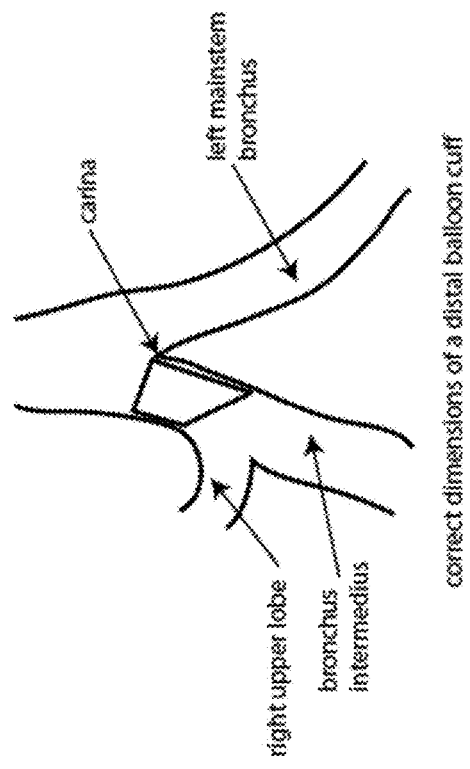
Figure 15A
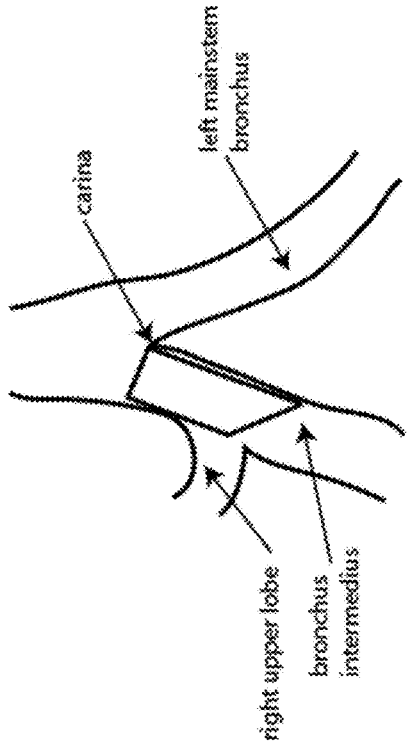
Figure 15B
Figure 15A – Figure 15C

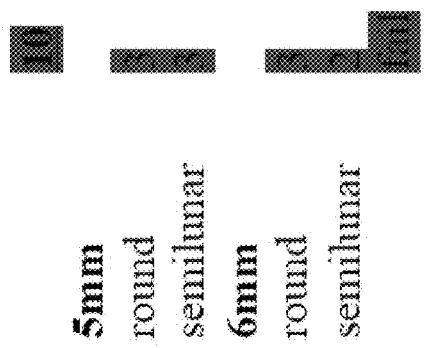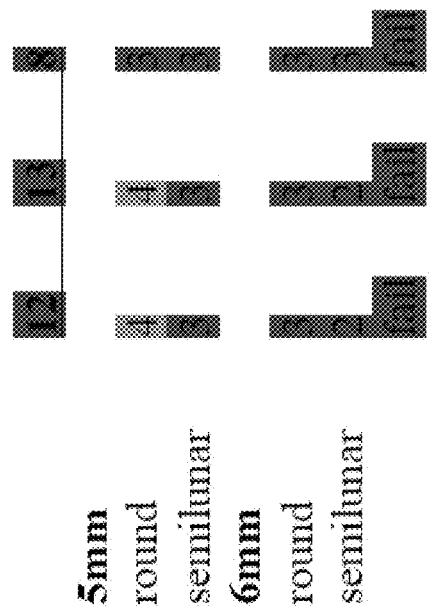
Figure 19

Side after cutting a few millimeters
Dimension

| | 1 | 2 | 3 | 4 | 5 | 6 | 7 | 8 | 9 | 10 |
|---|---|---|---|---|---|---|---|---|---|---|
| Sample 6 | 1.50 | 1.34 | 1.53 | 1.65 | 0.55 | 0.67 | 5.1 | 5.3 | 14.3 | 12.9 |
| Sample 12 | 1.45 | 1.36 | 1.57 | 1.63 | 0.54 | 0.66 | 5.1 | 5.4 | 13.9 | 12.6 |
| Sample 13 | 1.50 | 1.34 | 1.52 | 1.60 | 0.55 | 0.66 | 5.1 | 5.4 | 13.9 | 12.8 |
| Sample 14 | 1.49 | 1.39 | 1.54 | 1.59 | 0.54 | 0.66 | 5.1 | 5.4 | 13.8 | 12.6 |

Dimension #6 (membrane) – too thick
Dimension #7 (round lumen) – too short
Dimension #8 (semilunar lumen) – too tall
Dimension #9 (OD) – too large

Figure 22

70 Durometer w/clotstop

|  |  | sample1 | sample2 | sample3 | pre-soaked |
|---|---|---|---|---|---|
| 5mm | round | 5 | 5 | 5 | no change |
|  | semilunar | 1 | 1 | 1 | no change |
| 6mm | round | 5 | 5 | 5 | no change |
|  | semilunar | 1 | 1 | 1 | no change |

80 Durometer w/clotstop

|  |  | sample1 | sample2 | sample3 | pre-soaked |
|---|---|---|---|---|---|
| 5mm | round | 5 | 5 | 5 | no change |
|  | semilunar | 1+ | 1+ | 1+ | no change |
| 6mm | round | 5 | 5 | 5 | no change |
|  | semilunar | 1+ | 1+ | 1+ | no change |

90 Durometer w/clotstop

|  |  | sample1 | sample2 | sample3 | pre-soaked |
|---|---|---|---|---|---|
| 5mm | round | 5- | 5- | 5 | no change |
|  | semilunar | 1 | 1 | 1 | no change |
| 6mm | round | 5- | 5- | 4+ | no change |
|  | semilunar | 1 | 1 | 1 | no change |

Figure 23

DUAL LUMEN ENDOBRONCHIAL TUBE DEVICE

CROSS-REFERENCE TO RELATED APPLICATIONS

This application is a continuation-in-part of U.S. patent application Ser. No. 13/829,509, filed Mar. 14, 2013, which is entitled to priority to U.S. Provisional Patent Application No. 61/690,867, filed Jul. 6, 2012, the contents of which are each incorporated by reference herein in their entirety. This application is also entitled to priority to U.S. Provisional Patent Application No. 62/285,592, filed Nov. 3, 2015, which is incorporated herein by reference in its entirety.

BACKGROUND OF THE INVENTION

Lung isolation and single lung ventilation are routinely instituted during thoracic surgery. Surgery involving the lung or the contents of the thorax often requires cessation of ventilation to one lung for two main reasons: 1) to keep the lung immobile while surgery on it is performed and 2) to deflate the lung for better visualization of thoracic structures. Other indications for lung isolation include: 1) containment of unilateral pulmonary bleeding or infection, 2) management of bronchopleural fistula or other unilateral pulmonary air leaks, and 3) differential lung ventilation in the critical care setting. Today, the gold standard for lung isolation is the double lumen endobronchial tube (DLT). Modern disposable plastic DLTs are modifications of the original Robert-Shaw tube introduced more than sixty years ago. These endotracheal tubes contain two separate lumens, one for each lung, and ventilation is separated with the use of endotracheal and endobronchial balloon cuffs.

The DLT design suffers from several major drawbacks that negatively affect clinical care. The first is the large size of the tube, namely its effective outer diameter (OD). The four current adult-sized DLTs are 35, 37, 39, and 41 French in external circumference; this large size is needed to accommodate the necessary plastic structure and ventilation passages. Aside from being large, the DLTs are also reasonably stiff due to the plastic material used in their construction. Furthermore, the device's shaft is pre-bent into set angles designed to circumnavigate the anatomic curvature of the human airway. The combination of their large and bulky design and their stiffness with pre-set angles can lead to difficult insertion and even airway injury. Even if insertion is atraumatic, the DLT's large external diameter increases the pressure on the vocal cords, potentially injuring these delicate structures, especially during prolonged intubations. The pre-determined shaft angles are designed for the "average" person and do not necessarily match up with an individual patient's anatomy.

The second major design drawback is the relatively small size of the ventilation passages in the current DLT. Even the current bulky design houses two relatively small diameter channels, thus limiting the size of bronchoscopes, suction catheters, and other instruments that could be inserted into the lungs during use. No adult DLT sizes (35-41 Fr) can accommodate a pulmonary bronchoscope needed to perform diagnostic or therapeutic bronchoscopy (minimum 5.0 mm OD). If a diagnostic or therapeutic bronchoscopy exam is to be performed (e.g., suction/lavage, bronchial biopsy, bronchial laser) prior to surgical lung resection, a standard large bore endotracheal tube must first be utilized for this part of the procedure to accommodate the large bore bronchoscope. Once the bronchoscopy is completed, the endotracheal tube must be removed and a DLT put in its place, a procedure that can be fraught with risk. The limited lumen diameter of DLTs poses a special clinical challenge when a patient is bleeding from one lung and lung isolation is warranted. Although a DLT is ideal for lung isolation to prevent flooding the good lung with blood (possibly causing patient asphyxiation and death), placement of a DLT severely limits one's ability to perform the diagnostic and therapeutic bronchoscopy necessary to treat this medical emergency. Furthermore, the standard DLT's small airways essentially disqualify it from being used in the intensive care unit (ICU) setting given the need for intermittent and repeating bronchoscopy and airway suctioning (pulmonary toilet).

A third major limitation is that the DLT's long tube length combined with its small diameter lumens make even a small bronchoscope (4.0 mm OD) difficult to insert due to significant friction between the scope shaft and tube inner diameter (ID). Successful bronchoscope insertion requires repeated application of lubricant to the scope shaft, utilizing either water-based or other (e.g., silicone-based) lubricants. Because these lubricants inevitably dry up or get consumed in the process of the examination, the bronchoscope is often difficult to slide in the device and may even sustain damage or become stuck in the tube shaft.

A fourth major limitation of the standard DLT is that its tracheal and bronchial balloon cuffs are the standard elliptical shape with smooth surfaces. Once inflated, and in the moist setting of the human airway, these balloons easily slip, leading to device dislodgement. Movement of 10 mm or even less can lead to clinically significant device malpositioning. Such dislodgement can be at a minimum a significant disruption to the surgery given the loss of lung isolation, and at the extreme can cause severe life threatening hypoxemia (from obstructed oxygen flow and/or lung contamination). Given the unstable nature of the device's positioning, clinicians are trained to continuously evaluate the device's position within the airway to ensure that it does not dislodge.

A fifth significant limitation is that the DLT comes in two different configurations, left-sided and right-sided, depending on which bronchus the distal tip is expected to reside in. Although the majority of cases utilize a left-sided tube, for technical reasons a right-sided tube may need to be used, and in rare cases it is not clear at the beginning of the case which type of tube would best fit a particular patient. Because all four adult sizes (35, 37, 39, 41 Fr) must be available in a left- or right-sided configuration, the inventory must contain 8 different device sizes/configurations for adult patients, making device selection as well as inventory management a challenge.

A sixth significant limitation involves the need for clamping one limb of a standard Carlens Y adapter to initiate one lung ventilation (OLV). This standard adapter serves the usual dual function of 1) allowing for simultaneous ventilation of both lumens with one ventilator and 2) allowing for bronchoscopy to be performed during positive pressure ventilation. Traditionally, the anesthesiologist would borrow a stainless steel surgical clamp from the field to physically clamp and occlude the appropriate limb of the Y adapter. The weight of this clamp would often torque the whole tube assembly and cause a dislodgement. Although attaching an integrated plastic tubing clamp onto the Y-piece could be a logical solution, this would require two clamps to be integrated into the device (one on each limb). Changing from one external clamp to two integrated clamps raises the potential risk that both clamps are simultaneously closed accidentally, as could happen when the ventilation is switched from one lung to the other. Failure to recognize this error could lead to severe hypoxemia and even death caused by the inability to ventilate the patient and the lack of recognition that this is a device malfunction and not a patient complication.

A seventh significant limitation is the inability to directly measure the pressure in the balloon cuffs. Often, the balloons have to be inflated taut to prevent unintended lung inflation during OLV, especially the bronchial cuff. The lack of being able to measure the real time pressure in the balloon cuff puts the patient at potential risk of tracheal/bronchial injury.

There is a need in the art for improved dual lumen endobronchial devices. The present invention meets this need.

SUMMARY OF THE INVENTION

The present invention relates to a universal dual lumen endobronchial device, comprising: a straight shaft having a proximal end and a distal end; a curved bronchial tube extending from the distal end of the straight shaft; a tracheal lumen within the shaft extending from the proximal end of the shaft to a tracheal lumen opening at the distal end of the shaft; a bronchial lumen within the shaft extending from the proximal end of the shaft to a bronchial lumen opening at a distal end of the bronchial tube; a tracheal balloon cuff proximally adjacent to the tracheal lumen opening; and a bronchial balloon cuff proximally adjacent to the bronchial lumen opening; wherein the straight shaft and the curved bronchial tube are constructed from a polymer having a Shore A hardness between 60 and 95.

In one embodiment, the proximal end of the straight shaft comprises a Y-connector fluidly connected to the tracheal lumen and the bronchial lumen. In one embodiment, the straight shaft further comprises one or more inflation lumens fluidly connected to the tracheal balloon cuff, the bronchial balloon cuff, or both.

In one embodiment, the tracheal lumen and the bronchial lumen are separated by a flexible semilunar membrane, such that the cross-sectional area of the tracheal lumen and the bronchial lumen are substantially equal. In one embodiment, the semilunar membrane has a convex side adjacent to the tracheal lumen and a concave side adjacent to the bronchial lumen. In one embodiment, the semilunar membrane has a convex side adjacent to the bronchial lumen and a concave side adjacent to the tracheal lumen. In one embodiment, the semilunar membrane has a thickness between 0.45 and 0.55 mm.

In one embodiment, the tracheal lumen and the bronchial lumen are enclosed by a shaft wall having a thickness between 1 and 2 mm. In one embodiment, the tracheal balloon cuff and the bronchial balloon cuff comprise one or more raised ridges. In one embodiment, the tracheal balloon cuff has a cylindrical shape.

In one embodiment, the bronchial balloon cuff has a trapezoidal side profile having a long side and a short side substantially in parallel and a beveled side, such that the long side faces a medial direction toward the device's tracheal lumen opening, the short side faces a lateral direction opposite from the tracheal lumen opening, and the beveled side is adjacent to the device's bronchial lumen opening and faces the bronchial lumen opening in a lateral direction away from the tracheal lumen opening.

In one embodiment, the tracheal lumen and the bronchial lumen comprise a lubricant layer. In one embodiment, the lubricant layer is water activated. In one embodiment, the lubricant layer comprises polyvinylpyrrolidine (PVP). In one embodiment, the exterior of the straight shaft and the curved bronchial tube comprise a lubricant layer.

In one embodiment, the device further comprises at least one pressure sensor. In one embodiment, the device further comprises at least one flow sensor. In one embodiment, the device further comprises at least one temperature sensor. In one embodiment, the device further comprises at least one $CO_2$ sensor.

In another aspect, the present invention relates to a double clamp device, comprising: a planar frame having first and second adjacent slots forming first, second and third tube engagement positions; wherein the first slot is sized to restrict flow through a tube in the first tube engagement position, and the second slot is sized to permit flow through a tube in the first tube engagement position; wherein the first slot is sized to permit flow through a tube in the second tube engagement position, and the second slot is sized to permit flow through a tube in the second tube engagement position; and wherein the first slot is sized to permit flow through a tube in the third tube engagement position, and the second slot is sized to restrict flow through a tube in the third tube engagement position. In one embodiment, the device further comprises one or more grips.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 7A and FIG. 7B depict a comparison between an exemplary universal balloon cuff design of the invention (FIG. 7A) and a traditional balloon cuff design (FIG. 7B). The curve represents the position of a subject's medial bronchial wall after insertion of the respective devices into the left mainstem bronchus (LMB), especially when the patient is positioned with his or her left side down and the mediastinal contents shift down against the distal tip.

FIG. 8A and FIG. 8B depict additional universal balloon cuff designs. FIG. 8A is a parallelogram design. FIG. 8B is a curved design.

FIG. 12 depicts examples of a traditional right-sided double lumen endobronchial tube and a traditional left-sided double lumen endobronchial tube.

FIG. 15A depicts the placement of an ideal balloon cuff.

FIG. 15B and FIG. 15C depict the placement of poorly dimensioned balloon cuffs. FIG. 15B depicts a balloon cuff that is too long and partially occludes the right upper lobe. FIG. 15C depicts a balloon cuff that is too short; while it does not occlude the right upper lobe, the short length reduces contact surface and increases the likelihood of dislodgement.

FIG. 19 depicts the results of experiments investigating the effectiveness of several prototype versions of 80 durometer dual lumen endobronchial tube (DLT) main shafts that did not achieve exact dimensions as per the design.

FIG. 22 depicts the measurements of dimensions of the numerous prototype DLT shafts tested.

FIG. 23 depicts the results of investigating numerous prototype DLT shafts having multiple durometers and grooved internal diameters.

DETAILED DESCRIPTION

Figure 1:
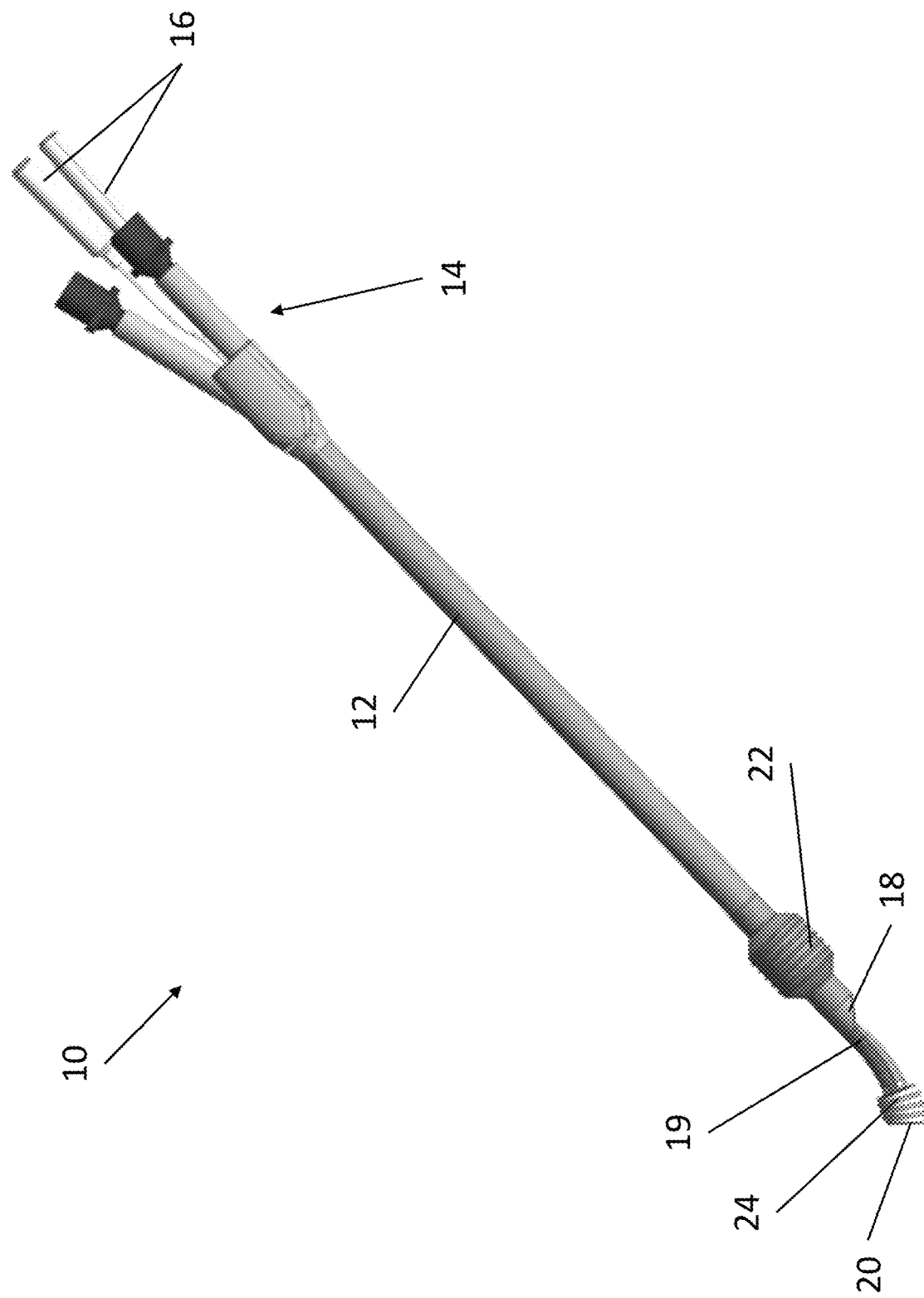
FIG. 1 depicts an exemplary double lumen endobronchial tube.

The present invention provides improved dual lumen endobronchial tube devices. The dual lumen endobronchial tube devices feature a universal design for left or right mainstem bronchus insertion. The dual lumen endobronchial tube devices also feature enhanced balloon cuff designs to minimize dislodgement while maintaining proper airway sealing. The present invention also provides improved integrated double clamps that prevent the accidental clamping of both tubes of a Y-adapter.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Dual Lumen Endobronchial Tube

The present invention provides dual lumen endobronchial tube devices that improve upon the limitations of traditional devices. The devices of the present invention feature a universal design for left and right mainstem bronchus insertion. The devices feature improved balloon cuffs for enhanced fit. The devices feature a semilunar membrane to enable the insertion of larger diameter instruments than traditional devices having comparable dimensions. The devices feature lubricant layers for ease of insertion.

Figure 2:
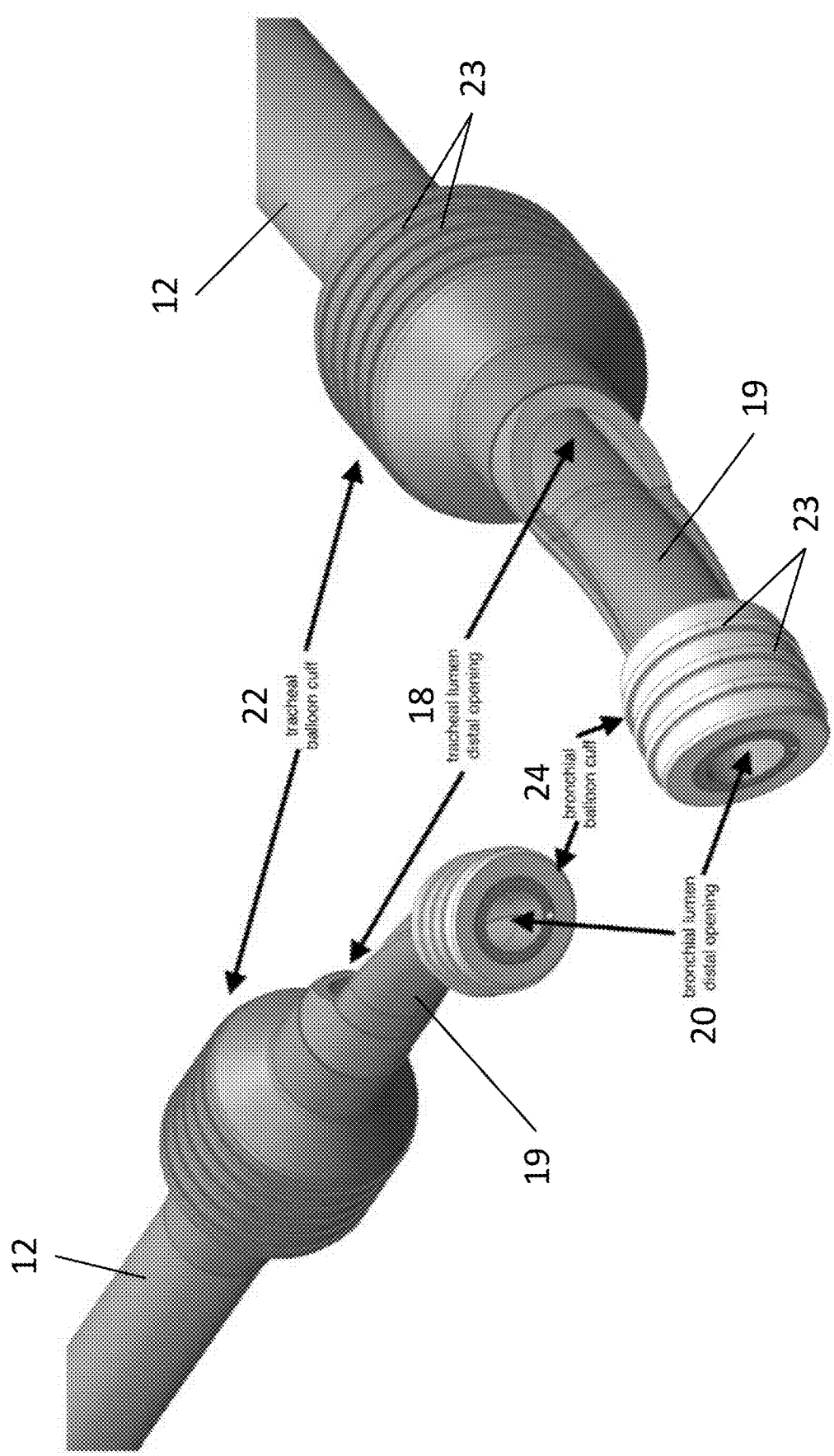
FIG. 2 depicts the distal tip of an exemplary double lumen endobronchial tube.
Figure 3:
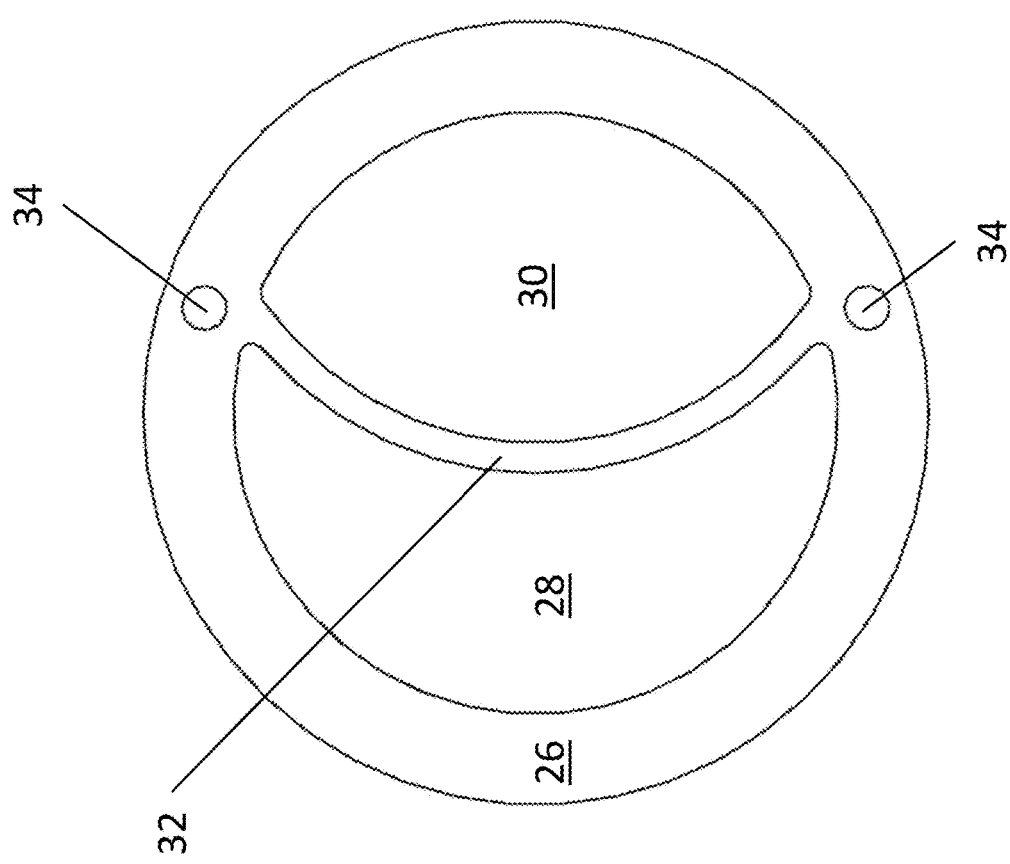
FIG. 3 depicts a cross-sectional diagram of the main shaft of an exemplary double lumen endobronchial tube.

Referring now to FIG. 1 and FIG. 2, an exemplary dual lumen endobronchial tube device 10 is depicted. Device 10 comprises an elongate shaft 12 having a longitudinal axis, a proximal end, and a distal end. The proximal end of device 10 comprises Y-connector 14 and pilot balloon/fill valve assembly 16. In some embodiments, the proximal end may further comprise an endotracheal tube holder/bite block for enhanced placement security (not shown). The distal end of device 10 comprises tracheal opening 18, bronchial tube 19, bronchial opening 20, tracheal balloon cuff 22, and bronchial balloon cuff 24. Referring now to FIG. 3, a cross-sectional diagram of shaft 12 is depicted. Shaft 12 comprises shaft wall 26 enclosing tracheal lumen 28, bronchial lumen 30, and semilunar membrane 32 separating tracheal lumen 28 and bronchial lumen 30. Shaft 12 further comprises inflation lumens 34.

As described elsewhere herein, in humans, the right mainstem bronchus (RMB) takes a more direct (less angled) takeoff from the trachea, whereas the left mainstem bronchus (LMB) in comparison takes a more angled takeoff as it comes off the trachea. For this reason, traditional DLT devices comprise two different designs, a L-sided and a R-sided DLT, which separately incorporate the different angles (FIG. 12). The stiff plastic of traditional DLTs make them a best fit for only their respective side. In contrast, shaft 12 and bronchial tube 19 of the present invention diverge from traditional endobronchial tube devices for universal insertion into either the LMB or the RMB. Shaft 12 is completely straight. Bronchial tube 19 has a slight preset curved edge to correctly line up with either the LMB or the RMB. In certain embodiments, bronchial tube 19 has a preset curve that is less curved than a traditional L-sided DLT bronchial tube and more curved than a traditional R-sided DLT bronchial tube. In certain embodiments, bronchial tube 19 has a preset curve that is biased closer to the curve of a traditional L-sided DLT bronchial tube than the curve of a traditional R-sided DLT bronchial tube. Shaft 12 and bronchial tube 19 can be constructed from any suitably soft and flexible material, such as silicone, polyvinyl chloride (PVC), and the like. In some embodiments, shaft 12 and bronchial tube 19 are constructed from a silicone having a Shore A hardness between 60 and 95. Shaft 12 and bronchial tube 19 are thereby soft and pliant enough to navigate the bends of a subject's trachea and mainstem bronchi and to avoid causing physical trauma to the lining of the subject's trachea and mainstem bronchi. In certain embodiments, shaft 12 and bronchial tube 19 are also rigid enough to prevent buckling, folding, or kinking when inserted into a patient's airway. In some embodiments, shaft 12 and bronchial tube 19 are stiff enough to be inserted without the aid of a stylet. However, it should be understood that shaft 12 and bronchial tube 19 are amenable to accepting a stylet.

Figure 4:
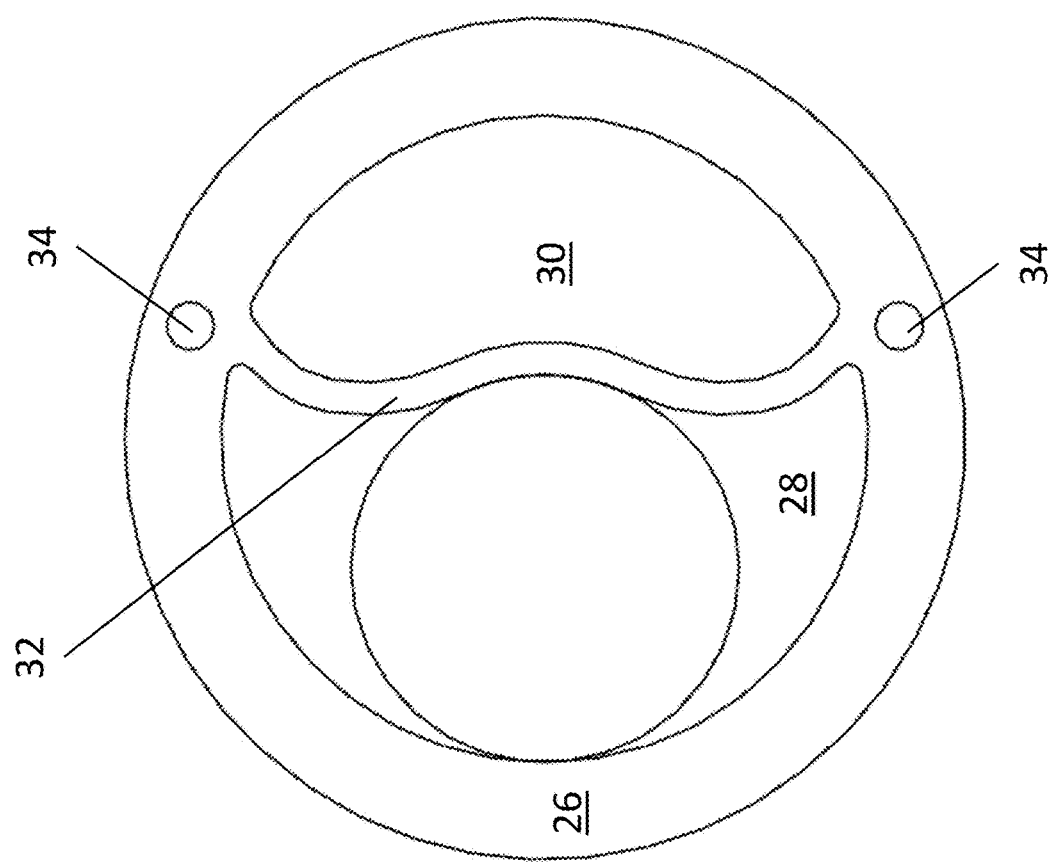
FIG. 4 depicts a cross-sectional diagram of the main shaft of an exemplary double lumen endobronchial tube showing the insertion of a large bronchoscope.

As described above, the cross-sectional diagram of device 10 depicts the multitude of lumens running through the length of shaft 12 enclosed by shaft wall 26. At the center of shaft 12 runs semilunar membrane 32. Semilunar membrane 32 separates tracheal lumen 28 from bronchial lumen 30. Semilunar membrane 32 is shaped such that the convex side of semilunar membrane 32 is adjacent to tracheal lumen 28 and the concave side of semilunar membrane 32 is adjacent to bronchial lumen 30. In some embodiments, semilunar membrane 32 can be shaped such that the convex side of semilunar membrane 32 is adjacent to bronchial lumen 30 and the concave side of semilunar membrane 32 is adjacent to tracheal lumen 28. Semilunar membrane 32 is flexible and may deform by inverting convexity when large diameter instruments are inserted into the narrower convex side (FIG. 4). In various embodiments, semilunar membrane 32 may be inelastic or semi-elastic. Semilunar membrane 32 is positioned such that the convex lumen and the concave lumen possess the same cross-sectional area. Inflation lumens 34 are positioned within shaft wall 26. Tracheal lumen 28 extends from a first opening of Y-connector 14 and terminates with tracheal opening 18. Bronchial lumen 30 extends from a second opening of Y-connector 14 and terminates with bronchial opening 20. Inflation lumens 34 each extend from a pilot balloon/fill valve assembly 16 to tracheal balloon cuff 22 or bronchial balloon cuff 24.

In certain embodiments, the dimensions of shaft 12 are provided within certain ranges for enhanced performance. Constructing shaft 12 within the following dimensions enables shaft 12 to be pliant and adapt to the curvature of a subject's airway, while retaining enough thickness to prevent kinking during use, which may cut off air supply to a subject. An exemplary thickness of shaft wall 26 can range between 1 and 2 mm. An exemplary outer diameter (OD) of shaft 12 can range between 12 and 14 mm. An exemplary thickness of semilunar membrane 32 can range between 0.45 and 0.55 mm; while semilunar membrane 32 may be constructed with different thicknesses, a construction thicker than the stated range may negatively affect ease of deformation, and a construction thinner than the stated range may lead to tearing and perforations caused by inserted instruments. An exemplary inner diameter (ID) of inflation lumens 34 can be 0.75 mm. Inflation lumens 34 may be positioned in any suitable part of shaft wall 26. In one embodiment, inflation lumens 34 are positioned at the intersection between shaft wall 26 and semilunar membrane 32. From a manufacturing perspective, this area allows for placement of inflation lumens 34 in the thickest, most substantial part of shaft wall 26, which prevents 1) partial formation with inflation lumens 34 breaking out through the edge of shaft wall 26 and 2) wandering of the location of inflation lumens 34, which can occur during the high pressure that occurs in extrusion during device construction. An exemplary device 10 constructed with the abovementioned dimensions enables the insertion of at least a 6.0 mm OD instrument into tracheal lumen 28 and the insertion of at least a 5.0 mm OD instrument into bronchial lumen 30. The overall OD of device 10 can be equivalent to the smallest traditional adult dual lumen endobronchial tube (DLT) (35 Fr) while having a functional ID greater than even the largest traditional adult DLT (41 Fr), which cannot accommodate an instrument larger than 4.5 mm OD.

Device 10 is secured within the trachea and bronchus of a subject by way of tracheal balloon cuff 22 and bronchial balloon cuff 24. Tracheal balloon cuff 22 is positioned just proximal to tracheal opening 18, forming an airtight seal between tracheal opening 18 and the non-intubated mainstem bronchus. Bronchial balloon cuff 24 is positioned at the proximal end of the bronchial opening 20, forming an airtight seal between bronchial opening 20 and the intubated mainstem bronchus. In some embodiments, tracheal balloon cuff 22 and bronchial balloon cuff 24 comprise one or more ridges 23 for enhanced grip (FIG. 2). Tracheal balloon cuff 22 can have any suitable shape commonly used in the art. In some embodiments, tracheal balloon cuff 22 is substantially cylindrical.

Figure 5:
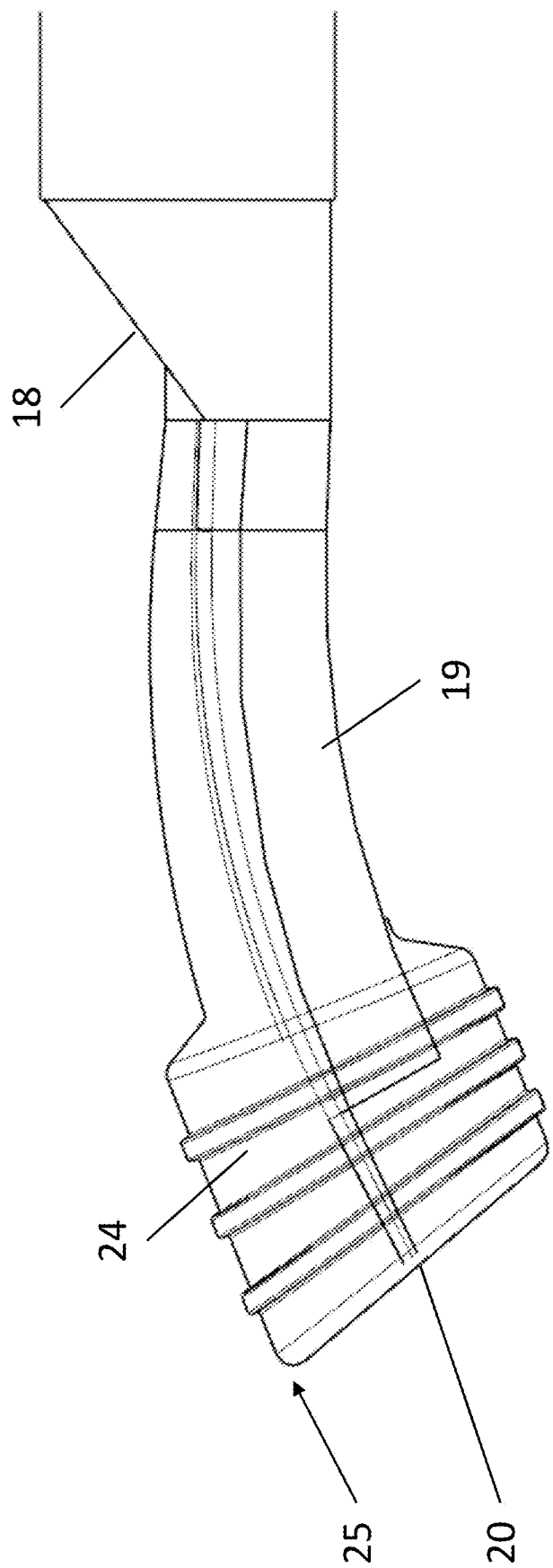
FIG. 5 depicts an exemplary universal bronchial balloon cuff.

In certain embodiments, bronchial balloon cuff 24 comprises a universal design suitable for both LMB and RMB intubation. Referring now to FIG. 5, a side profile view of an exemplary universal bronchial balloon cuff 24 is depicted. The side profile view of bronchial balloon cuff 24 comprises a substantially trapezoidal shape having a long side and a short side substantially in parallel and a beveled side adjacent to bronchial opening 20 facing a distal direction. Preferably, the short side is oriented in the direction of the curve of bronchial tube 19, and the long side terminating in distal tip 25 is oriented in the direction of tracheal opening 18. When inserted into a patient, the short side of the trapezoidal profile faces the lateral direction abutting the lateral wall of the mainstem bronchus opposite the tracheal carina (the bifurcation of the trachea into the two mainstem bronchi), while the long side of the trapezoidal profile faces the medial direction abutting the mainstem bronchus just beyond the tracheal carina. The beveled side of the trapezoidal side profile faces the lobar bronchi openings in a lateral direction, away from the midline." Bronchial balloon cuff 24, while substantially trapezoidal in profile, preferably is cylindrically shaped to maximize surface contact with an airway, as depicted in FIG. 2.

Figure 6:
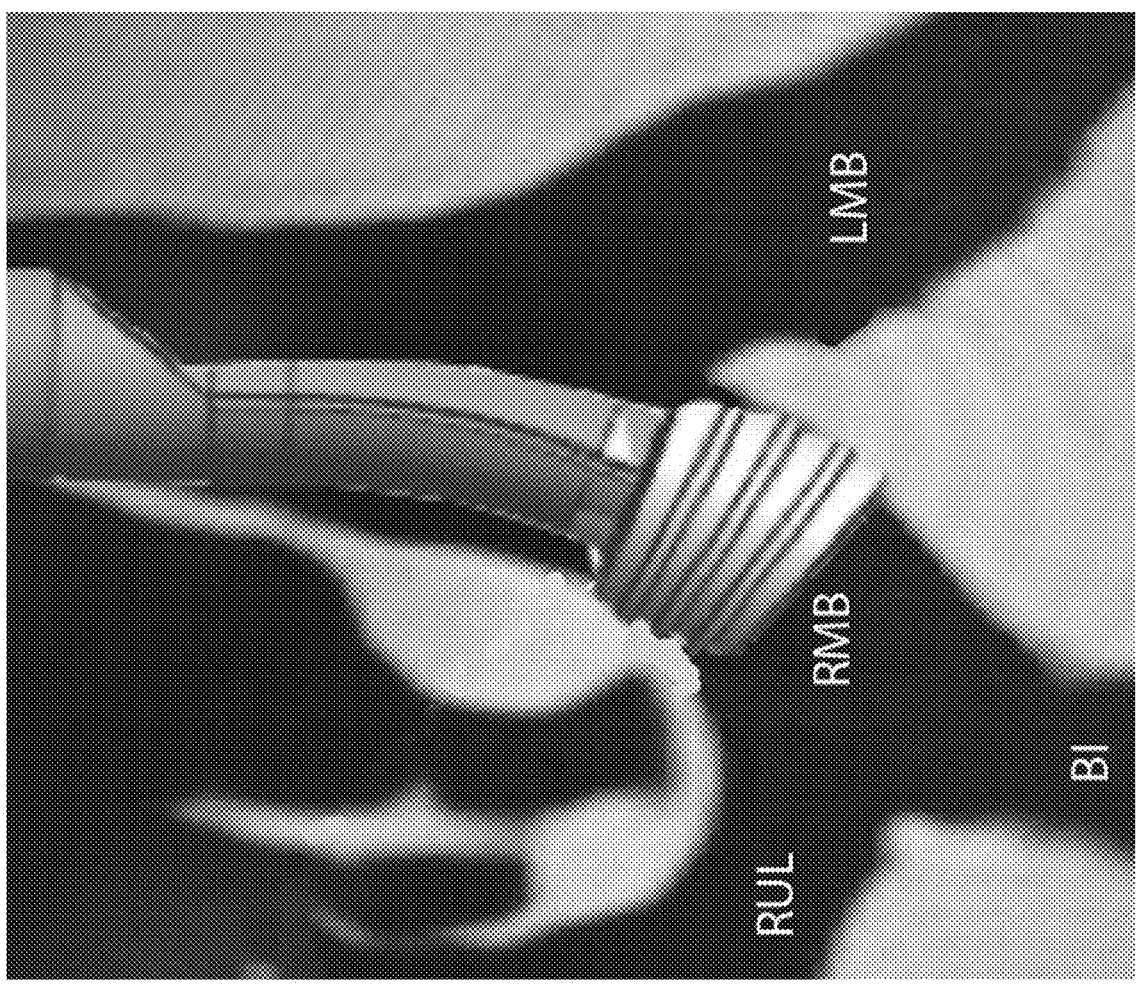
FIG. 6 depicts the insertion of an exemplary universal balloon cuff into a right mainstem bronchus (RMB). Abbreviations: left mainstem bronchus (LMB); right upper lobe (RUL); bronchus intermedius (BI).

The advantageous aspect of shaping bronchial balloon cuff 24 with a substantially right trapezoid side profile can be seen in FIG. 6. Anatomically, the RMB is shorter than the LMB. To be a truly universal design, the right trapezoid side profile enables bronchial balloon cuff 24 to securely fit in both the RMB and the LMB. As shown in FIG. 6, a properly oriented device 10 places the long side of bronchial balloon cuff 24 against the carina, or the medial side of the tracheal bifurcation, for greater surface area grip and traction. The short side is placed against the right mainstem bronchus lateral wall, facing the right upper lobe (RUL) takeoff. On average, the RMB is only about 15 mm long, and can be as short as 10 mm or less, and the short side is specially designed to securely fit against this short distance without occluding airways. The beveled side thereby faces laterally, pointing bronchial opening 20 towards the bronchial airways for unobstructed airflow.

Another advantageous aspect of shaping bronchial balloon cuff 24 with a substantially right trapezoid side profile can be seen in FIG. 7. Regardless of whether device 10 has been inserted into the LMB or RMB, proper placement will always cause the beveled side to orient bronchial opening 20 toward the bronchial airways. FIG. 7 illustrates a simulated insertion of device 10 into a LMB (FIG. 7A) next to a simulated insertion of a traditional device into a LMB (FIG. 7B). The curved red line represents the LMB medial wall. It is clear from FIG. 7 that with the unique right trapezoidal construction of bronchial balloon cuff 24, the beveled side faces laterally and points bronchial opening 20 away from the airway wall and towards the distal airway, while the traditional device comprises a bevel that is oriented in the opposite, medial direction, and is partially occluded by the airway wall. This is especially important when considering certain operations orient a subject on his or her left side, such as in right sided lung surgery. The weight of the heart and mediastinal structures pushes on the airway, which in certain subjects leads to the medial wall of the left mainstem bronchus pushing against and occluding the bronchial opening of a traditional device.

As will be understood by those having skill in the art, a universal bronchial balloon cuff 24 is not limited to a substantially right trapezoidal design. Non-limiting universal designs for bronchial balloon cuff 24 include any trapezoidal design, a parallelogram design (FIG. 8A), and a curved design (FIG. 8B). The commonly shared feature among the different universal designs is a distal tip 25 adjacent to a beveled or angled face.

In various embodiments, the devices of the present invention further comprise a lubricant coating. The lubricant coating can be placed on the outside of the device (e.g., the exterior of shaft 12, bronchial tube 19), on the inside of the device (e.g., the inner surface of tracheal lumen 28, bronchial lumen 30), or both. The lubricant coating can aid in the insertion of the devices into the airways of a subject. The lubricant coating can also aid in the insertion of various instruments into the device tracheal lumen and bronchial lumen. The lubricant coating, being bonded to the device, avoids the need to continuously add lubricant during use. In certain embodiments, the lubricant coating is water activated and hydrophilic, wherein the addition of small amounts of water or saline to the lubricant coating creates a very slick surface with a low frictional coefficient. The lubricant coating resists quick drying and is resilient, such that it remains bonded to the device during use. The lubricant coating can be any suitable lubricant coating. In some embodiments, the lubricant coating comprises polyvinylpyrrolidine (PVP). In some embodiments, the lubricant coating further comprises an antibiofilm or antibacterial material.

In various embodiments, the devices of the present invention further comprise one or more sensors for various detection means. For example, in one embodiment, an exemplary device 10 further comprises one or more pressure sensors. The pressure sensors can provide a real-time measurement of the tracheal balloon cuff pressure, the bronchial balloon cuff pressure, or both. In some embodiments, the pressure sensors display whether the pressure is in a safe range or in an unsafe, over-inflated range. The display can be digital (LCD, LED) display or an analog (gauge) display. Additional non-limiting examples of sensors include flow sensors, temperature sensors, $CO_2$ sensors, and the like.

Double Clamp

The present invention also provides a double clamp that improves upon the limitations of traditional devices. The double clamp allows an operator to switch between clamping the two tubes of a Y-adapter without the risk of accidentally clamping both tubes at the same time.

Figure 9:
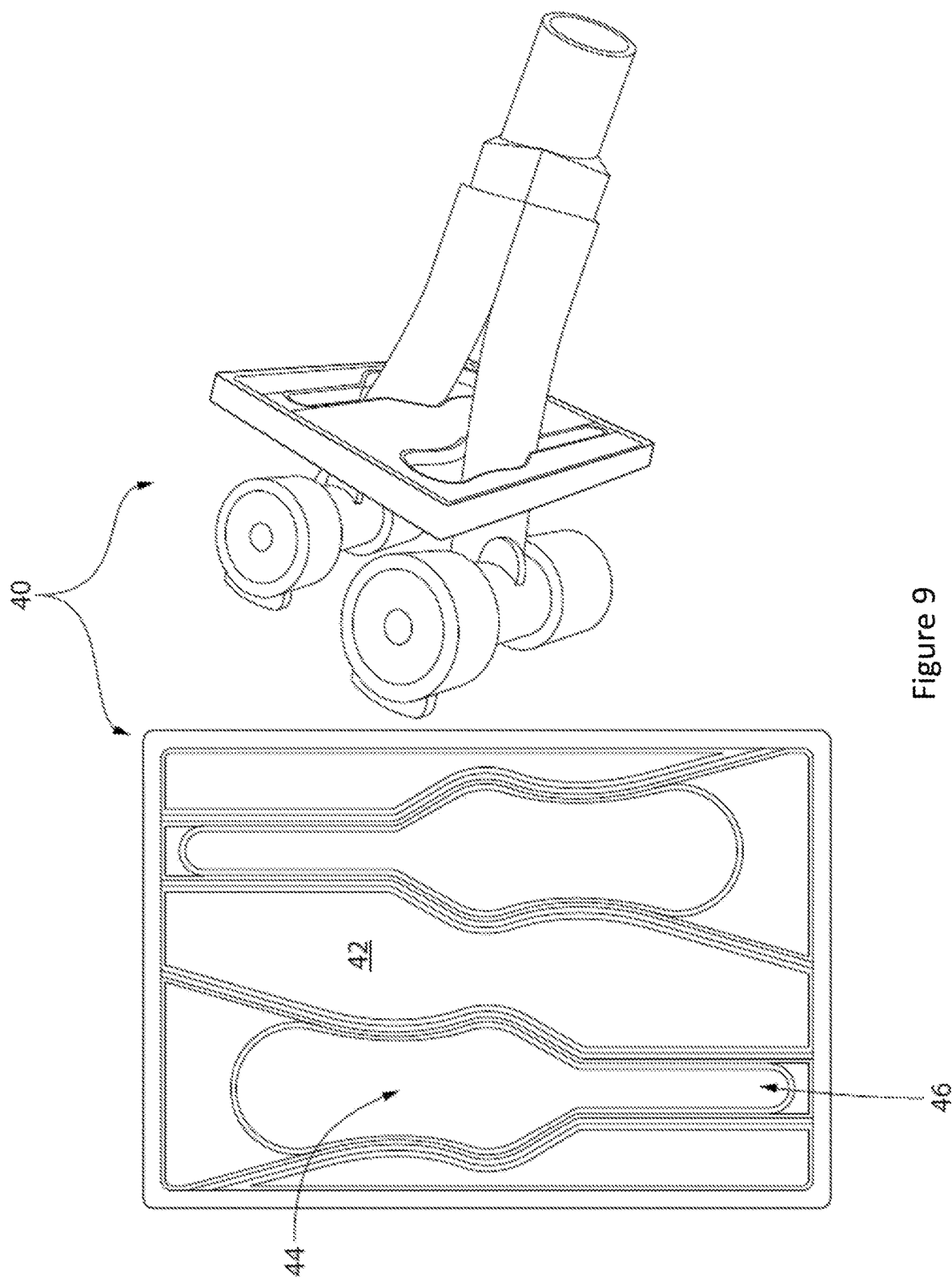
FIG. 9 depicts an exemplary double clamp and exemplary use.

Referring now to FIG. 9, an exemplary double clamp 40 is depicted. Double clamp 40 comprises frame 42 and a first and a second, oppositely oriented tube hole, each having an open region 44 and a restricting region 46. The opposite orientation of the two tube holes is such that open region 44 of the first tube hole is adjacent to restricting region 46 of the second tube hole, and the open region 44 of the second tube hole is adjacent to restricting region 46 of the first tube hole. A portion of the open region 44 of the first and the second tube hole overlap in the middle of frame 42.

The two tubes of a Y-adapter may be inserted into the first and the second tube holes of double clamp 40 such that the tubes rest in the middle of frame 42, wherein the open region 44 of the first and the second tube hole overlap. The tubes may be individually clamped by pushing one of the two tubes into a restricting region 46 of a tube hole. Y-adapters are constructed with the two tubes adjacent to each other. Therefore, pushing one of the two tubes into a restricting region 46 of a tube hole thereby requires that the adjacent tube be pushed into the open region 44 of the adjacent tube hole. As a result, it is unlikely that both tubes of a Y-adapter are simultaneously pushed into a restricting region 46, which would dangerously cut off all airflow to a subject.

In another embodiment, double clamp 40 can be described as a planar frame having first and second adjacent slots forming first, second and third tube engagement positions, wherein the first slot is sized to restrict flow through a tube in the first tube engagement position, and the second slot is sized to permit flow through a tube in the first tube engagement position; wherein the first slot is sized to permit flow through a tube in the second tube engagement position, and the second slot is sized to permit flow through a tube in the second tube engagement position; and wherein the first slot is sized to permit flow through a tube in the third tube engagement position, and the second slot is sized to restrict flow through a tube in the third tube engagement position.

Figure 10:
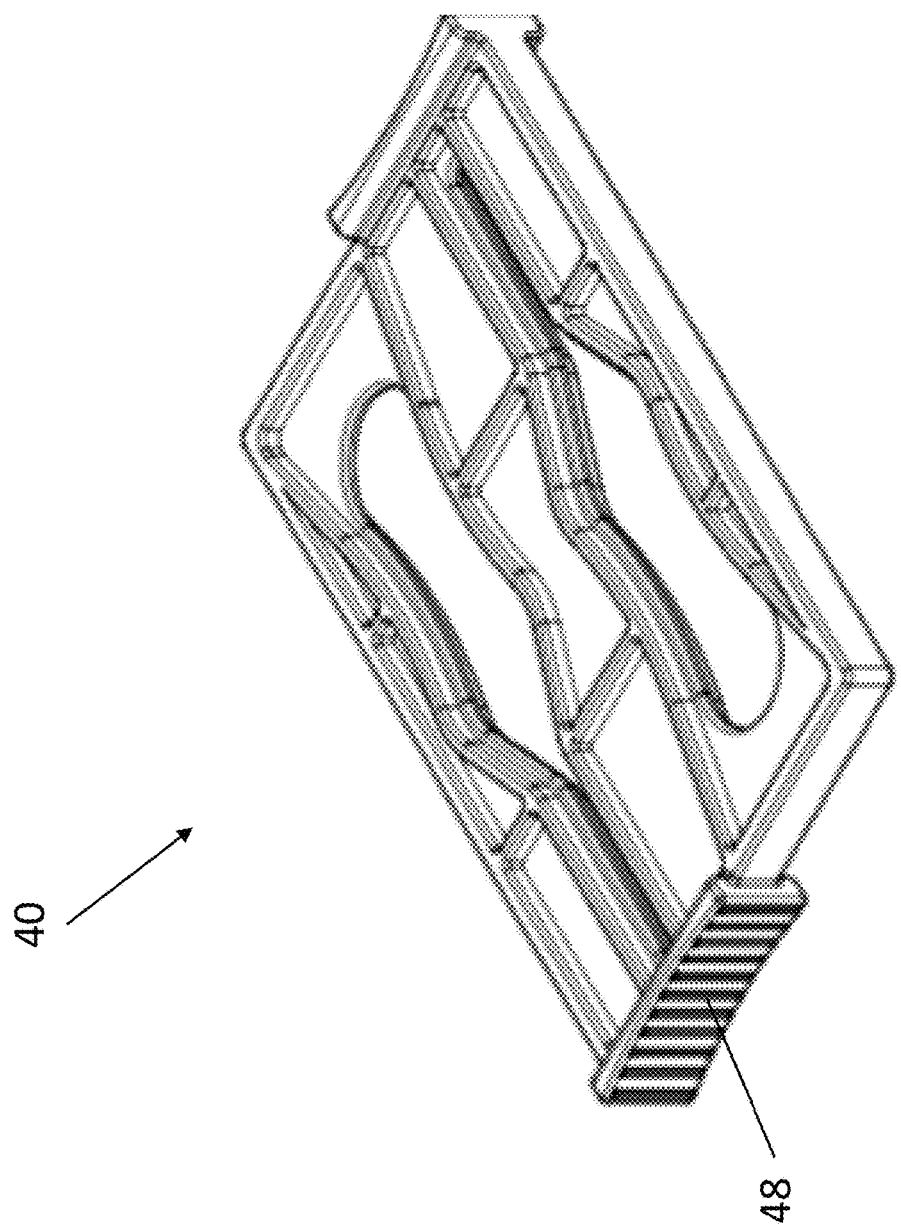
FIG. 10 depicts an exemplary double clamp having grips.

Double clamp 40 can be constructed from any suitable material, such as a metal, a hard plastic, or a rigid but slightly pliant plastic. In some embodiments, double clamp 40 is provided as a standalone clamp to be installed onto any suitable Y-adapter tube. In other embodiments, double clamp 40 is preassembled around Y-adapter tubes for use with any suitable ventilation device. In some embodiments double clamp 40 further comprises one or more features that enhance ergonomics, such as grips 48 (FIG. 10).

The devices of the present invention can be made using any suitable method known in the art. The methods may vary depending on the materials used. For example, devices substantially comprising a plastic or polymer may be milled from a large block or injection molded. Likewise, devices substantially comprising a metal may be milled, cast, etched, or deposited by techniques such as chemical vapor deposition, spraying, sputtering, and ion plating. In some embodiments, the devices may be made using 3D printing techniques commonly used in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, utilize the present invention and practice the claimed methods. The following working examples therefore, specifically point out the preferred embodiments of the present invention, and are not to be construed as limiting in any way the remainder of the disclosure.

Example 1

Distal Balloon Cuff Development

Figure 11:
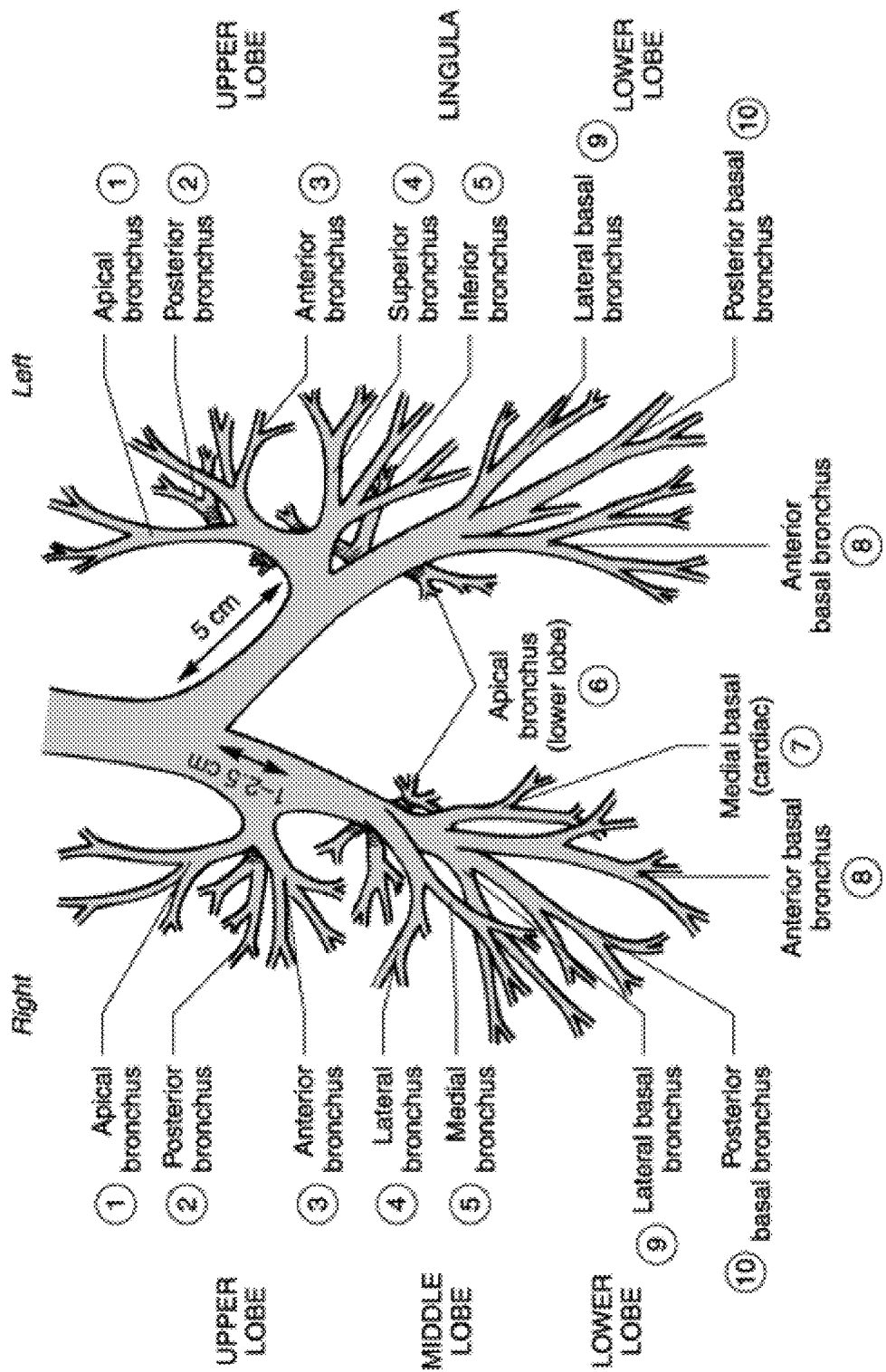
FIG. 11 depicts the anatomy and average dimensions of the left and right mainstem bronchus.

A double lumen endotracheal tube (DLT) contains a distal component that sits in the mainstem bronchus. A balloon cuff is inflated to create an air seal necessary for positive pressure ventilation. There are two configurations: a left sided configuration and a right sided configuration. They are named based on the mainstem bronchus that the distal component resides. Because the anatomy of the left and right-sided mainstem bronchus differs, the design of the distal component, including the balloon cuff, also differs. The right mainstem bronchus is short as compared to the left mainstem bronchus, and if the left DLT distal component design were to be used in the right mainstem, it would likely occlude the opening to the right upper lobe. For this reason, a different design, encompassing an off center balloon cuff with a side peering orifice, is used for the R sided DLT. See FIG. 11 for details about right vs. left bronchus, and FIG. 12 for traditional DLT right and left designs.

The present study investigates the design of a distal component that will fit into the right mainstem bronchus without occluding the right upper lobe (RUL). At the same time, the component must fit in a secure fashion, so that it does not easily dislodge out of the bronchus and into the trachea. Therefore, a balance is needed wherein the tip is not too long, but at the same time, has enough length to make proper surface contact such that friction holds it in place. The balloon cuff must occlude the bronchus completely so that there are no air leaks. Finally, the distal component must also fit into the left mainstem bronchus, and align the device's bronchial opening with the lobar airways.

Figure 13:
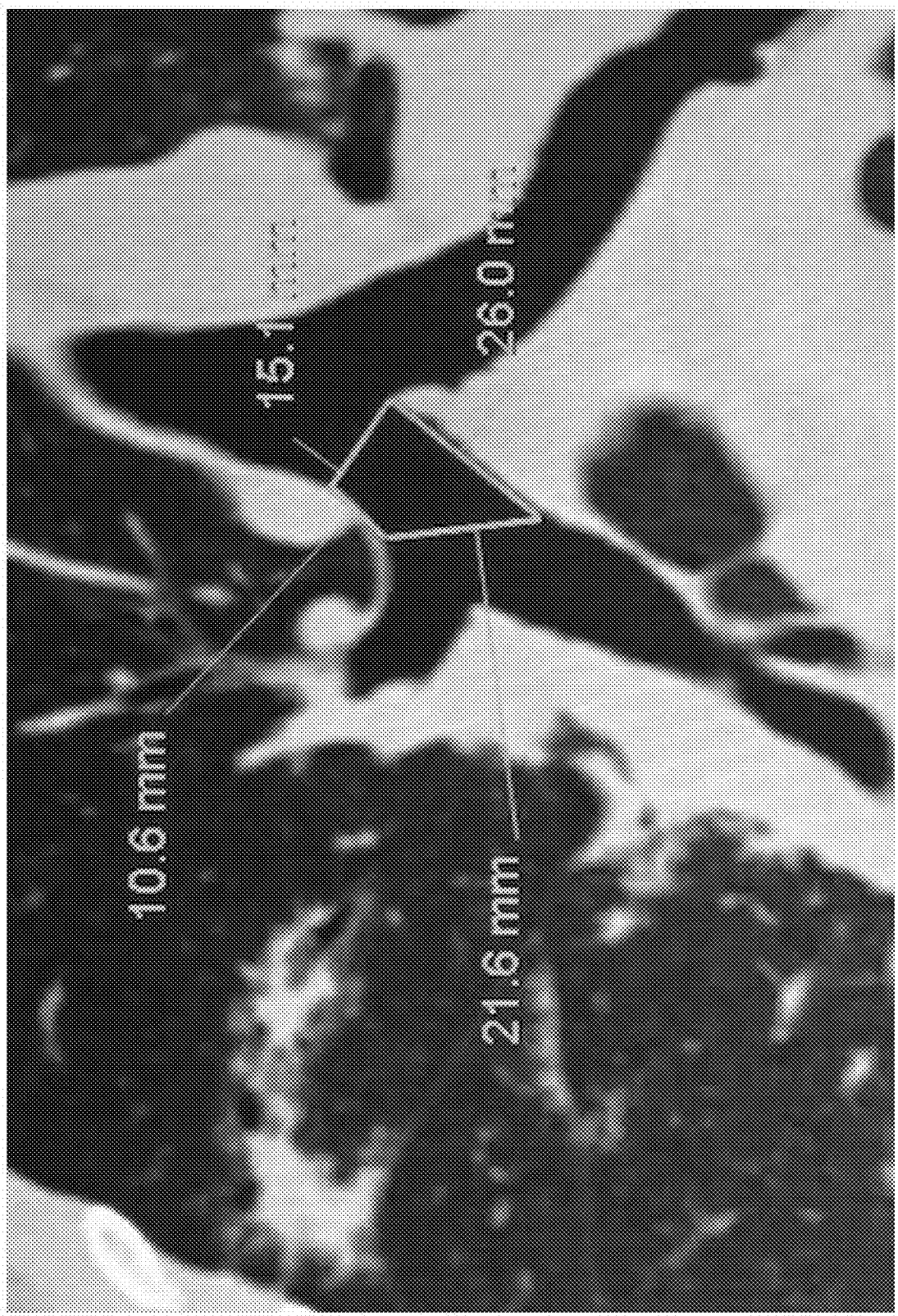
FIG. 13 depicts a CT scan of a right mainstem bronchus and its exemplary dimensions (in one individual patient).
Figure 14:
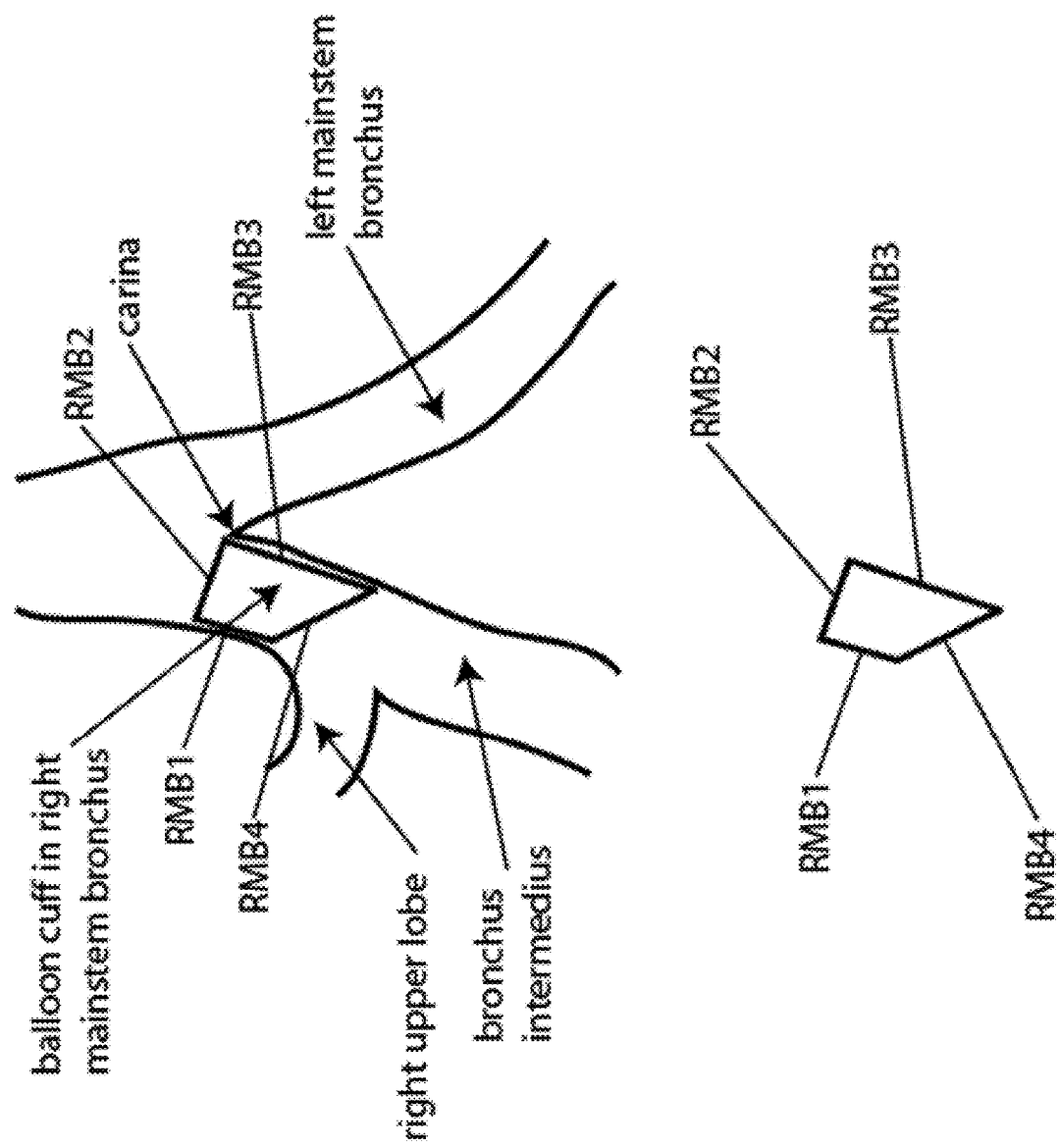
FIG. 14 depicts the construction of an ideal balloon cuff.

The present research makes use of collected airway anatomy data from nearly 200 patients of differing age, weight, height, race, etc., with the purpose of representing a heterogeneous population. Next, the right mainstem bronchus (RMB) was identified from CT images, and its relevant dimensions measured (FIG. 13). FIG. 14 is a schematic that illustrates the airway anatomy, the location of the balloon cuff, and the relevant nomenclature (naming of the dimensions). The data was then analyzed statistically in order to get a better sense of the variability between patients. This data was then compared to previously published data describing human trachea and mainstem bronchi dimensions, and the entire combined data set utilized in designing the bronchial cuff Given that the design will have to fit in nearly all patients, this data was examined to better understand the extreme values that are seen in some patients. In particular, a short right mainstem bronchus is the main challenge, as it does not leave adequate room to position the distal member appropriately.

In each CT cut, the following lines were drawn and dimensions measured: 1) RMB1, 2) RMB2, 3) RMB3, 4) RMB4 (see FIG. 13). RMB1 is the length of the RMB on the RUL side. RMB2 is the diameter of the RMB from the tip of the carina drawn perpendicularly to the opposing wall of the RMB. RMB3 is the length of the RMB on the carina side. RMB4 is the diagonal line that connects the distal ends of RMB1 and RMB3 together (FIG. 14). All dimensions were measured in millimeters. The dimensions were drawn as closely as possible to the anatomy, with the limitation that the anatomy was not always amenable to straight lines given variability and other circumstances.

The RMB is shorter than the LMB because of the anatomic takeoff of the RUL. Specifically, the official length of the RMB is RMB1, as measured in the CT cuts. It is this dimension that limits the length of the balloon cuff, as a balloon that is too long could occlude the opening of the RUL when positioned in the RMB. FIG. 15A through FIG. 15C illustrate this point. FIG. 15A demonstrates the ideal dimensions of the balloon cuff; RMB1 reaches up to but does not cross the RUL bronchus takeoff. FIG. 15B illustrates an example where the balloon is too long and crosses the RUL takeoff, thus occluding the RUL from ventilation. FIG. 15C shows a balloon cuff that is too short relative to the RMB. Although it does not obstruct ventilation, it is not ideal because its contact surface at the short (RMB1 dimension) is minimized, as well as its friction with the airway. This deficiency could make the cuff more likely to dislodge. Furthermore, the shorter the cuff, the higher the probability that small dislodgements will disrupt lung isolation, as it will temporarily disengage from the RMB inlet and break the bronchial airway seal. Thus, an ideal balloon cuff would have the longest possible dimensions of RMB1 while still fitting into the vast majority of patients without obstructing the RUL takeoff.

Given these limitations in RMB anatomy, the CT data was collected in a group of heterogeneous surgery patients with the goal of better elucidating the relevant dimensions accurately. Previous attempts to do so relied on bronchoscopy derived or post-mortem measurements, which are inherently subjective and/or inaccurate. Any patients with abnormally distorted anatomy were excluded, as would occur with a large tumor. Below is Table 1 containing a summary of the findings:

TABLE 1

| N = 193 | RMB1 (mm) | RMB2 (mm) | RMB3 (mm) | RMB4 (mm) |
|---|---|---|---|---|
| Average | 14.0 | 13.8 | 24.1 | 18.7 |
| Maximum | 24.4 | 21.1 | 36.1 | 27.0 |
| Minimum | 6.6 | 6.8 | 10.4 | 10.4 |
| STD DEV | 3.8 | 2.3 | 4.7 | 3.2 |
| RMB1# < 10 mm | 26 | | | |
| RMB1# < 9 mm | 13 | | | |
| RMB1# < 8 mm | 4 | | | |
| RMB1# < 7 mm | 1 | | | |

An exemplary balloon cuff should encompass the following dimensions: 1) a short side of 10 mm in length, 2) a long side of 15 mm in length, 3) a beveled edge that connects the short side and the long side, and 4) an inflation to neutral (non-stretched) diameter of 24 mm.

If this device were to be tested on the patient population (n=193) that was studied, this balloon would fit well into nearly all patients' RMB. Specifically, the current balloon cuff dimensions are expected to be a good fit for 188 patients, a marginal fit for 3 patients, and a poor fit for 2 patients. Even in the marginal and poor fit patients, the device is very likely to still function properly in the RMB, as gas flow is still able to navigate corners and angles, and even partially obstructed airways will still be able to receive gas-flow. These performance statistics are better than those of the current right-sided DLT designs.

Once a prototype of this balloon shape is developed, in vitro as well as in vivo tests (animal studies first, then human studies) would be needed to determine both its ability to fit in the RMB as well as to seal the RMB and isolate the lung. A preliminary study fitted a prototype of this balloon shape with a standard ETT shaft into a cadaver airway, and the results indicated that the prototype balloon shape fit well.

Ideally, the balloon would collapse as flat as possible when deflated, and inflate such that the short side and the long side are flat and make maximal contact with the bronchial surface (like a tire), rather than having a curvature (radius). Also ideally, the texture of the balloon surface would be somewhat "roughened", such that it would not become slippery when wet. This would aid in keeping the balloon in place by increasing the friction at the contact surface between the balloon and the bronchial wall. Given that static friction between two objects is the frictional coefficient multiplied by perpendicular force, clinical practice has been to maximally inflate balloons to increase the perpendicular force given the very low frictional coefficient. If a balloon has a higher friction coefficient, the cuff could be inflated less as a bigger force would not be needed, thus potentially reducing airway mucosal ischemia and injury.

Example 2

Membrane Durability Test

The present study examines the durability of a 0.5 mm semilunar membrane in response to puncture from endotracheal tube stylets or other sharp, hard objects inserted into the lumen of an endotracheal tube.

Figure 16:
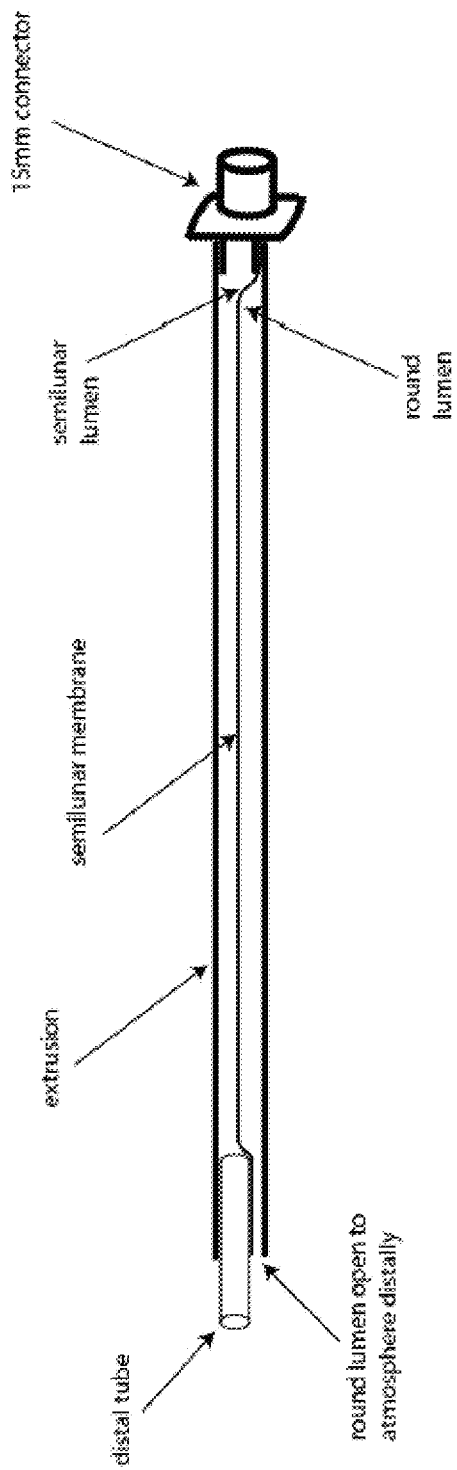
FIG. 16 depicts an experimental setup to test the durability of the semilunar membrane.
Figure 17:
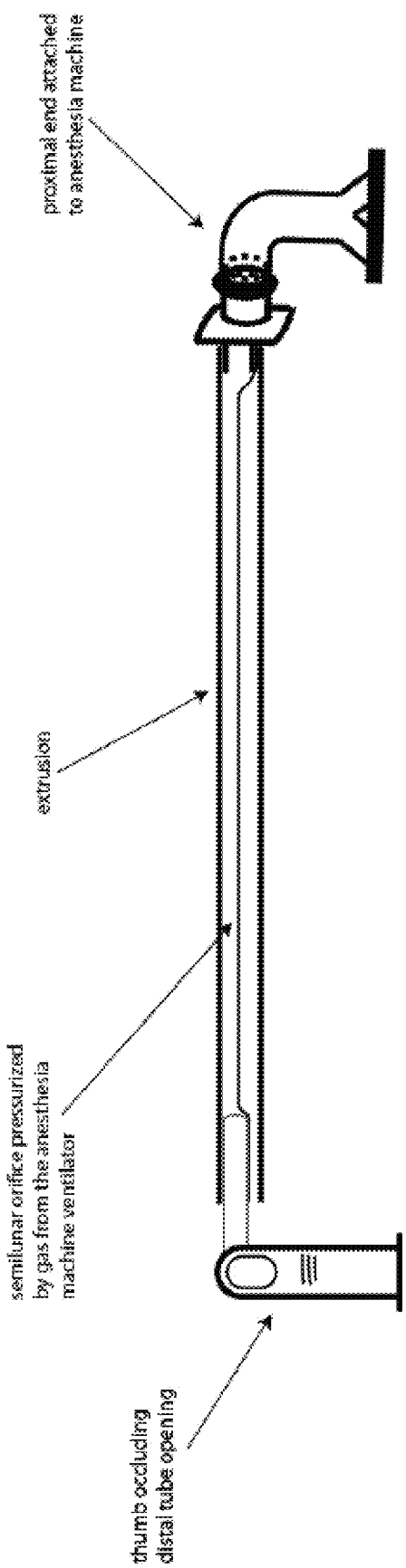
FIG. 17 depicts a further experimental setup to test the durability of the semilunar membrane.
Figure 18:
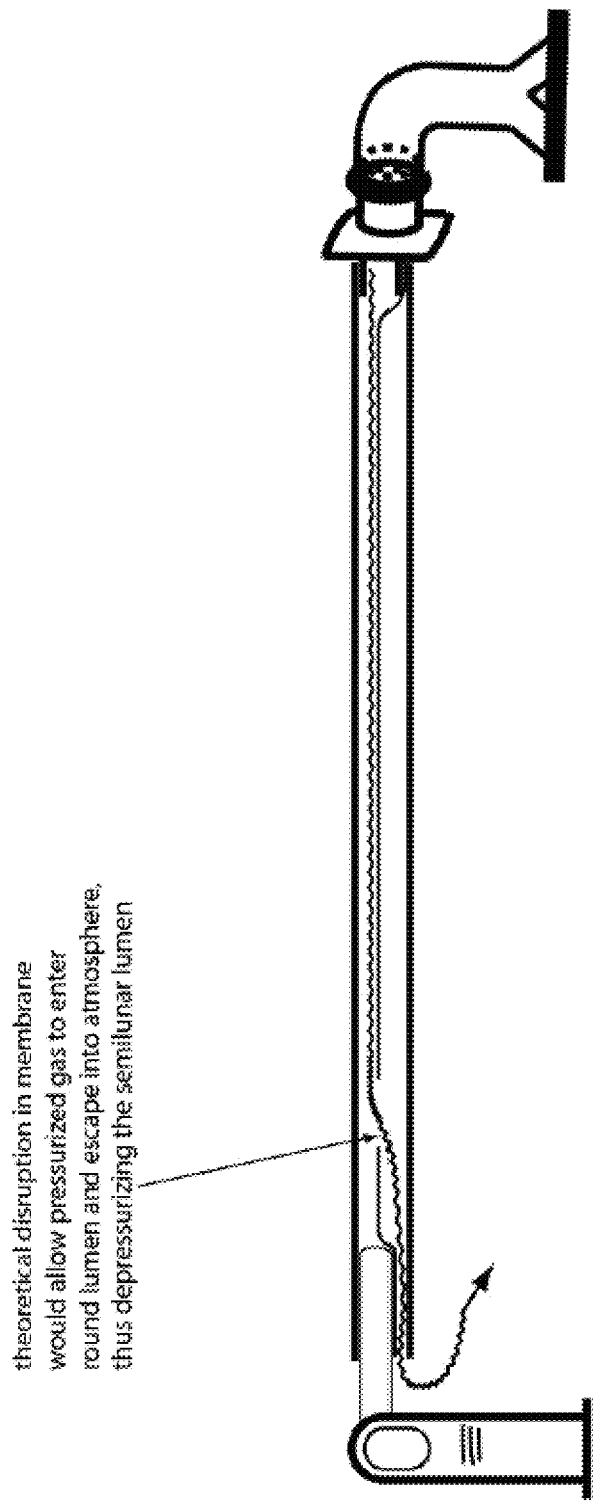
FIG. 18 depicts a further experimental setup demonstrating a hypothetical failure in the durability of the semilunar membrane.

The semilunar orifice is tested given that it has the smallest inner diameter (ID) and needs to deform to accept a stylet, maximizing the friction and thus the chance that the membrane will perforate. The full-length extruded shaft with lubricious coating applied to the internal diameter of both lumens was tested, although the device was dry to maximize friction and to take the coating out of the equation. A 15 mm universal connector was attached to the proximal end of the semilunar lumen, completely obliterating both lumens on that side. On the distal end, a round tube was inserted such that the other lumen (round) is still patent and in continuity with the atmosphere, and the connection between the tube and semilunar lumen was silicone sealed to prevent leak (FIG. 16). The proximal connector was then connected to an anesthesia machine. With the thumb sealing the distal end, the pressure was slowly ramped to determine that there is no leak and that the membrane does not perforate or fail at pressure FIG. 17. Once this was completed, the aluminum stylet to be used in the final device was introduced in a rough fashion numerous times. The stylet tips were bent at increasing angles, beyond what would be done in clinical practice, to simulate extremely rough handling of the endotracheal tube. At the extreme, the stylet tip was bent at around 35 degrees such that it would just barely traverse the 15 mm connector. As the stylet exited the connector into the shaft, the tip was aimed directly into the semilunar membrane convexity to increase probability of a "stabbing" penetration into the divider. No lubrication or hydration was added during these insertions. After numerous insertions, the device was pressure tested again. Any small perforations would cause a leak as the pressurized air would enter the round lumen through the perforation and then exit the atmosphere through the distal round lumen aperture (FIG. 18).

Initial pressurization: the device was pressurized on the anesthesia machine to a pressure of 75 cmH$_2$O without any evidence of ill effects on the membrane. This is the maximum achievable pressure on the machine, and would be several times higher than would be clinically safe.

Rough stylet insertion: dozens of intentionally rough insertions were performed. After roughly a dozen, the device was pressure tested to 75 mmH$_2$O. This was repeated numerous times, with increasing roughness and stylet tip angling, to force the stylet tip to deform and drag against the convex side of the membrane. The membrane was observed to stretch at the initial contact point where the very bent stylet was pushing directly into it, before giving way and allowing the stylet to advance further into the shaft. Even at this maximal friction and angled rough insertion, the membrane did not tear. At no point did the membrane integrity become compromised.

In conclusion, the semilunar membrane is resistant to puncture and disruption. It easily absorbed punishment beyond what would be expected in clinical use without failing. Both high pressures from gas and angled uncoated aluminum stylets to be packaged with the product failed to damage its integrity.

Example 3

Testing Bronchoscope Extrusion 80 Durometer and 0.5 mm Dividing Membrane

The following study tests 80D semilunar lubricant-coated extrusions with co-extruded fill tubes n=16 from the same lot for performance using a 5 mm and 6 mm bronchoscope. The lot contains 50 units, 30 coated and 20 uncoated. 4 samples are tested in each of the 4 lubricating conditions outlined below, for a total of 16 samples tested.

The extrusions were prepared based on the following lubricating conditions: 1) extrusions 1-4: water based lubricant jelly on scope only+10 cc saline in extrusion ID (5 cc in each lumen); 2) extrusions 5-8: water based lubricant jelly on scope+extrusion submerged in water for 120 s; 3) extrusions 9-12: water based lubricant jelly on scope+10 cc saline in extrusion+water based lubricant jelly in extrusion ID; 4) extrusions 13-16: water based lubricant jelly on scope+ extrusion submerged in water+water based lubricant jelly in extrusion ID.

Extrusions were individually inspected by hand, and labeled #1-16, as described above. One extrusion from each group was measured for critical dimensions as previously described. Extrusions were visually inspected for imperfections and then tested as follows: 1) were lubricated in their respective manner; 2) both a 5 mm and 6 mm bronchoscope was inserted into both lumens; 3) ease of the insertion and removal tests was scored (5 point scale); 4) samples that were deemed inferior, likely due to the lubricating protocol, were then "rescued" by redoing the test with protocol #3 (the previous standard); 5) state of the coating (peeling, flaking) was examined.

The 5-point scale is as follows: 5—scope drops in with no resistance (full length of extrusion); 4—scope slides in with minimal resistance (minimal resistance at the last 10 cm); 3—scope inserts in with some resistance (some resistance at the last 10 cm); 2—scope inserts in with moderate resistance (resistance throughout insertion); 1—scope inserts in but cannot pass to the other end due to resistance; 0—scope only inserts a few cm and then stops due to friction. A sample must pass with all scopes easily passing all lumens to be considered a pass. The actual bronchoscope dimensions for the 5.0 mm was 6.0 mm, and for the 6.0 mm was 6.7 mm. Initial results are depicted in FIG. 19.

The testing was aborted after clinically testing a few samples as it was clear that the dimensions were not to specifications and that this alteration was significantly affecting the results. The results were reproducible among the 4 samples tested, and the measurements also suggested that there was little variability among the different samples. Four samples were measured with calipers (#6, 12, 13, 14), and they all had very similar dimensions.

Figure 20:
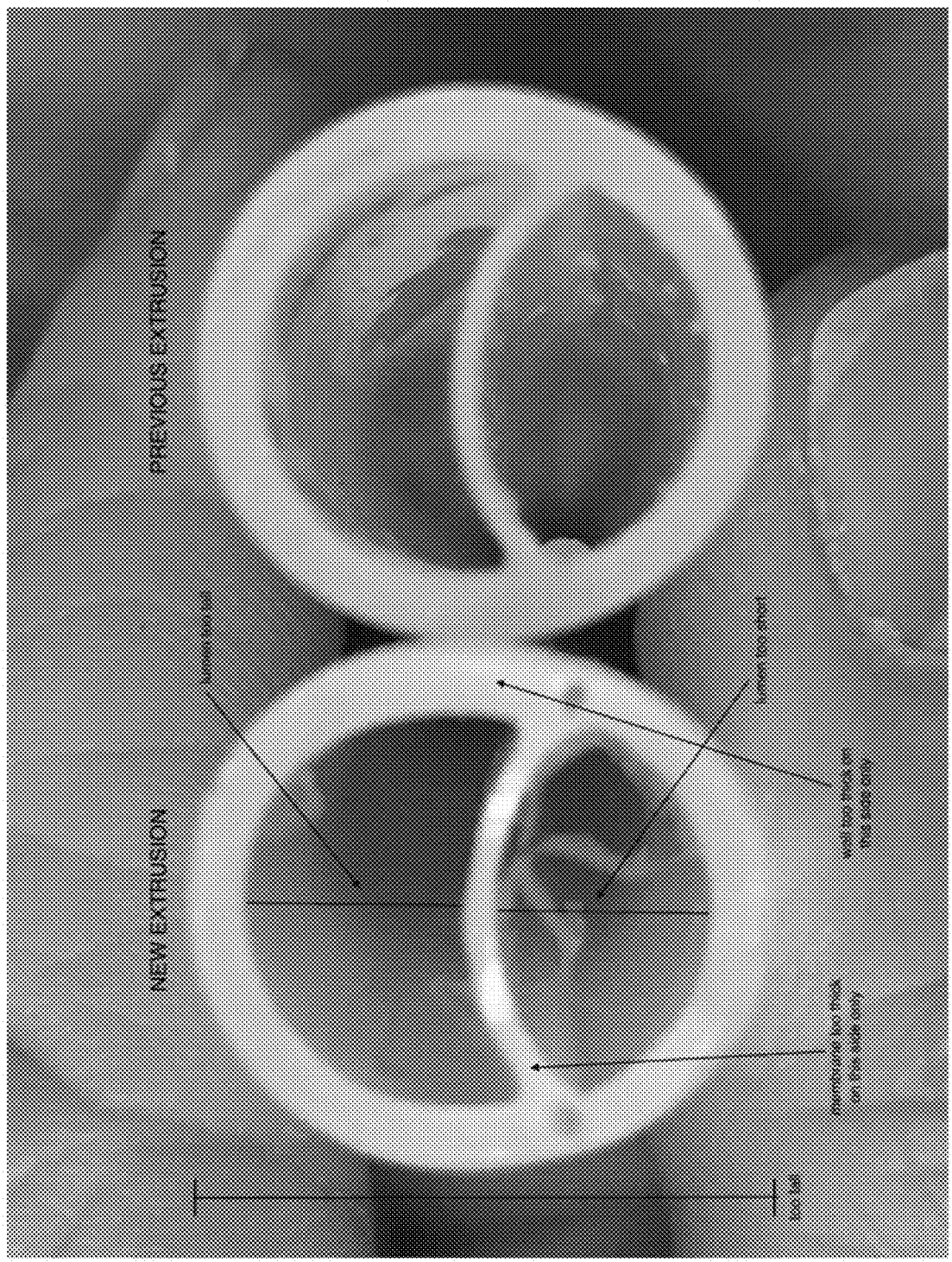
FIG. 20 depicts a comparison between two prototype DLT shaft dimensions.
Figure 21:
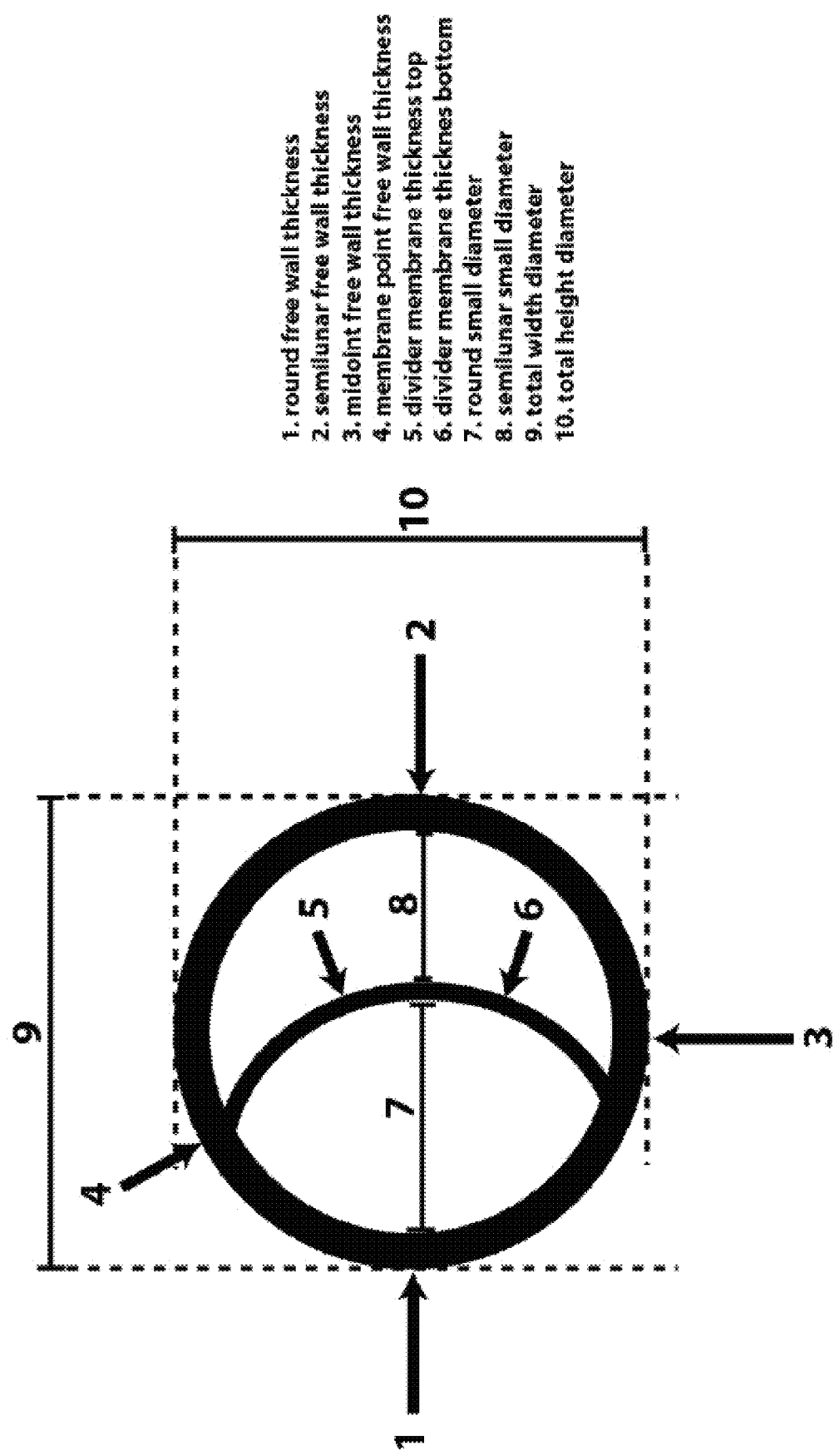
FIG. 21 depicts the measurements examined in the study investigating the accuracy of the dimensions of the numerous prototype DLT shafts tested.
Figure 24:
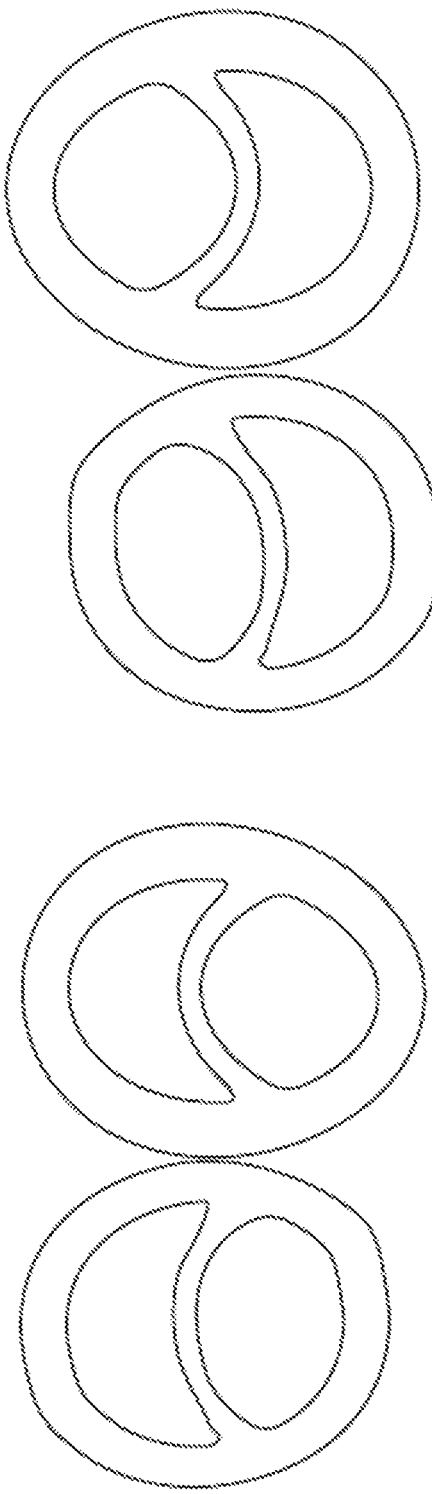
FIG. 24 compares several different DLT main shafts that did not achieve exact dimensions as per the design.

In conclusion, the performance of the extrusions was a failure compared to later prototype successful extrusions. The cause of the failure was obvious: the extrusion dimensions were not fully to specifications (please see FIG. 20 highlighting inaccuracies in the extrusion dimensions): the membrane was too thick on one end of the arch; the membrane was too flat, not arched enough; the outer walls were too thick in places; the overall shape was too elliptical; the round lumen was too short, and the semilunar lumen was too tall. The thickening of the inner membrane as well as the alternation of the lumen shapes directly contributed to the failure. The membrane was too rigid and short in curvature, such that it did not invert and deflect away from the scope, as it should when the scope was inserted into the semilunar lumen. The outer walls were too thick and rigid, and the membrane too short/thick such that the round lumen did not stretch to accommodate the large scope enough. The round lumen was too narrow and the semilunar was too wide, but even this increased width did not translate to a performance improvement because of the membrane's reduced compliance.

In addition, the following observations were made: the thickening of the membrane and outer walls was occurring near the area where the fill tubes were located; the elliptical nature of the extrusion was likely secondary to the thickening of the outer walls; the fill tubes appeared to be positioned well, although their patency was not tested; there was a longitudinal "striping" seen on the membrane along the length of the extrusion.

Example 4

Clinical Testing of Bronchoscope Extrusion with Multiple Durometers and Grooved Internal Diameter The following study compares three different durometers of extrusions 70, 80, and 90. Each sample was internally coated with water-activated lubricant. Three samples of each durometer were made for quality control testing. For this study, n=9 samples were tested (three from each durometer).

The testing began with lubrication of the 5 mm and 6 mm bronchoscope shafts with water based lubricant jelly. The actual measured diameters of the bronchoscope distal tips were 5.2 mm and 6.5 mm, respectively. 5 cc of saline was then flushed through each of the extrusion's lumens, and then water based lubricant jelly was squirted into the first 2 cm or so of the extrusion tube. The bronchoscopes were then inserted into the lumens and ease of passage was tested (see outline of steps below). Finally, one extrusion representing each durometer was then placed in a 1500 cc bottle of warm water such that the bottom ⅔ of the extrusion was submerged in water for a few minutes. The scopes were then inserted in both lumens again.

Extrusions were visually inspected for imperfections and then tested as follows: 1) wet with saline flush syringes (5 cc at a time) only; 2) water-based lubricant jelly was then added; 3) both a 5 mm and 6 mm bronchoscope was inserted into both lumens; 4) ease of insertion and removal were compared (5 point scale); 5) state of the coating (peeling, flaking) was examined.

The 5-point scale is as follows: 5—scope drops in with no resistance (full length of extrusion); 4—scope slides in with minimal resistance (minimal resistance at the last 10 cm); 3—scope inserts in with some resistance (some resistance at the last 10 cm); 2—scope inserts in with moderate resistance (resistance throughout insertion); 1—scope inserts in but cannot pass to the other end due to resistance; 0—scope only inserts a few cm and then stops due to friction. The results are depicted in FIG. 23.

The following observations were made: the dimensions of the extrusion were different from previous runs. Although the extrusion was never round in cross section (the design states 13 mm radius), three randomly selected samples from previous runs had the following elliptical diameters (mm): 1) 13.5×12; 2) 13.3×12; 3) 13.2×12.2. The first value represents the long diameter and the second represents the short diameter. The current extrusions were more elliptical than the previous ones, and also varied by durometer. The 70D diameters for the three samples were as follows (mm): 1) 14.0×11.8; 2) 14.3×11.9; 3) 14.2×12.0. The 80D diameters for the three samples were as follows (mm): 1) 14.5×12.2; 2) 14.7×12.4; 3) 14.6×12.3. The 90D diameters for the three samples were as follows (mm): 1) 13.9×11.9; 2) 13.9×11.9; 3) 13.6×11.9. The 90D samples were the least elliptical and most closely resembled the previous extrusions.

The wall thickness of the extrusion was supposed to be 1.5 mm, but in the present batch, the wall thickness varied. The 70D wall thicknesses were not measured. The 80D walls were thicker than they were supposed to be (see below). The 90D walls were the correct thickness.

The 80D wall thicknesses measured at each lateral free walls (value 1 and 2) and near the membrane junction (value 3) were as follows (mm): sample 1: 1) 1.67, 2) 1.86, 3) 2.00; sample 2: 1) 1.70, 2) 1.80, 3) 1.90; sample 3: 1) 1.60, 2) 1.70, 3) 1.90. The 90D wall thicknesses measured at each lateral free walls (value 1 and 2) and near the membrane junction (value 3) were as follows (mm): sample 1: 1) 1.40, 2) 1.50, 3) 1.50; sample 2: 1) 1.50, 2) 1.50, 3) 1.50; sample 3: 1) 1.50, 2) 1.50, 3) 1.60.

The grooves reduce the friction when the silicone is dry, but actually increase the friction when the silicone is lubricated, when compared to a control sample that has no grooves. This result was reproduced on the previous sample from which the grooves were modeled.

The results indicate: the extrusion should be round and have an OD of 13 mm; the extrusion ID should have a water-based lubricant coating; the extrusion ID should be completely smooth, without any grooves; the inner membrane works best when it is slick and flexible; the inner membrane must be able to deflect, but also resist kinking; the durometer needs to be at least 70D to resist shaft kinking; higher durometers improve kink resistance but limit membrane flexibility.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A universal dual lumen endobronchial device, comprising:
    a straight shaft having a proximal end and a distal end;
    a curved bronchial tube extending from the distal end of the straight shaft;
    a tracheal lumen within the shaft extending from the proximal end of the shaft to a tracheal lumen opening at the distal end of the shaft;
    a bronchial lumen within the shaft extending from the proximal end of the shaft to a bronchial lumen opening at a distal end of the bronchial tube;
    a tracheal balloon cuff proximally adjacent to the tracheal lumen opening; and
    a bronchial balloon cuff proximally adjacent to the bronchial lumen opening, the bronchial balloon cuff having a trapezoidal side profile with a long side and a short side substantially in parallel and a beveled side, such that the long side faces a medial direction toward the tracheal lumen opening, the short side faces a lateral direction opposite from the tracheal lumen opening, and the beveled side faces a lateral direction away from the tracheal lumen opening and is flush with the bronchial lumen opening;
    wherein the straight shaft and the curved bronchial tube are constructed from a polymer having a Shore A hardness between 60 and 95.

2. The device of claim 1, wherein the proximal end of the straight shaft comprises a Y-connector fluidly connected to the tracheal lumen and the bronchial lumen.

3. The device of claim 1, wherein the straight shaft further comprises one or more inflation lumens fluidly connected to the tracheal balloon cuff, the bronchial balloon cuff, or both.

4. The device of claim 1, wherein the tracheal lumen and the bronchial lumen are separated by a flexible semilunar membrane, such that the cross-sectional area of the tracheal lumen and the bronchial lumen are substantially equal.

5. The device of claim 4, wherein the semilunar membrane has a convex side adjacent to the tracheal lumen and a concave side adjacent to the bronchial lumen.

6. The device of claim 4, wherein the semilunar membrane has a convex side adjacent to the bronchial lumen and a concave side adjacent to the tracheal lumen.

7. The device of claim 4, wherein the semilunar membrane has a thickness between 0.45 and 0.55 mm.

8. The device of claim 1, wherein the tracheal lumen and the bronchial lumen are enclosed by a shaft wall having a thickness between 1 and 2 mm.

9. The device of claim 1, wherein the tracheal balloon cuff and the bronchial balloon cuff comprise one or more raised ridges.

10. The device of claim 1, wherein the tracheal balloon cuff has a cylindrical shape.

11. The device of claim 1, wherein the tracheal lumen and the bronchial lumen comprise a lubricant layer.

12. The device of claim 11, wherein the lubricant layer is water activated.

13. The device of claim 11, wherein the lubricant layer comprises polyvinylpyrrolidine (PVP).

14. The device of claim 1, wherein the exterior of the straight shaft and the curved bronchial tube comprise a lubricant layer.

15. The device of claim 1, further comprising at least one pressure sensor.

16. The device of claim 1, further comprising at least one flow sensor.

17. The device of claim 1, further comprising at least one temperature sensor.

18. The device of claim 1, further comprising at least one $CO_2$ sensor.

* * * * *